United States Patent
Duque et al.

(10) Patent No.: US 9,642,897 B2
(45) Date of Patent: May 9, 2017

(54) TREATMENT OF BONE DISEASES

(75) Inventors: Gustavo Duque, Cabarita (AU); Christopher Vidal, Ultimo (AU)

(73) Assignee: THE UNIVERSITY OF SYDNEY, Kingswood, New South Wales (AU)

( * ) Notice: Subject to any disclaimer, the term of this patent is extended or adjusted under 35 U.S.C. 154(b) by 0 days.

(21) Appl. No.: 14/344,702

(22) PCT Filed: Sep. 13, 2012

(86) PCT No.: PCT/AU2012/001095
§ 371 (c)(1),
(2), (4) Date: May 16, 2014

(87) PCT Pub. No.: WO2013/036998
PCT Pub. Date: Mar. 21, 2013

(65) Prior Publication Data
US 2015/0343037 A1    Dec. 3, 2015

(30) Foreign Application Priority Data
Sep. 13, 2011    (AU) ................................. 2011903764

(51) Int. Cl.
| | | |
|---|---|---|
| A61K 31/44 | (2006.01) |
| A61K 38/51 | (2006.01) |
| A61K 38/44 | (2006.01) |
| A61K 38/45 | (2006.01) |
| A61K 31/4402 | (2006.01) |
| A61K 38/21 | (2006.01) |

(52) U.S. Cl.
CPC .............. *A61K 38/51* (2013.01); *A61K 31/44* (2013.01); *A61K 31/4402* (2013.01); *A61K 38/217* (2013.01); *A61K 38/44* (2013.01); *A61K 38/45* (2013.01); *C12Y 113/11006* (2013.01); *C12Y 113/11011* (2013.01); *C12Y 113/11052* (2013.01); *C12Y 114/13009* (2013.01); *C12Y 401/01045* (2013.01)

(58) Field of Classification Search
CPC .... A61K 38/51; A61K 31/4402; A61K 31/44; A61K 38/44
USPC .......................................................... 514/354
See application file for complete search history.

(56) References Cited

U.S. PATENT DOCUMENTS

| | | | |
|---|---|---|---|
| 6,407,125 B1 | 6/2002 | Fernandez-Pol | |
| 6,579,891 B1 * | 6/2003 | Fernandez-Pol | ..... A61K 9/0043 514/354 |

FOREIGN PATENT DOCUMENTS

| | | |
|---|---|---|
| EP | 0 947 508 | 10/1999 |
| EP | 1 369 114 | 12/2003 |
| WO | 2007/081878 | 7/2007 |
| WO | 2008/054825 | 5/2008 |

OTHER PUBLICATIONS

Abstract of Ruffmann et al., Drugs Exp Clin Res., 1987;13(10):607-614.*

(Continued)

*Primary Examiner* — San-Ming Hui
(74) *Attorney, Agent, or Firm* — Tyler J. Sisk; Casimir Jones, S.C.

(57) ABSTRACT

The invention relates generally to the field of bone diseases. More specifically, the invention relates to methods and compositions for the treatment of osteoporosis and related disorders.

5 Claims, 9 Drawing Sheets

A

B

(56) References Cited

OTHER PUBLICATIONS

Duque, G., et al., "Interferon-gamma Plays a Role in Bone Formation In Vivo and Rescues Osteoporosis in Ovariectomized Mice," Journal of Bone and Mineral Research, Jul. 2011, vol. 26, No. 7, pp. 1472-1483.
Bianco, N. R., et al. "Therapeutic Effect ofExosomes From Indoleamine 2,3-Dioxygenase-Positive Dendritic Cells in Collagen-Induced Arthritis and Delayed-Type Hypersensitivity Disease Models," Arthritis and Rheumatism, Feb. 2009, vol. 60, No. 2, pp. 380-389.
Beninger, R.J., et al, "Picolinic acid blocks the neurotoxic but not the neuroexcitant properties of quinolinic acid in the rat brain: evidence from turning behaviour and tyrosice hydroxylase immunohistochemistry," Neuroscience, 1994, vol. 61, No. 3, pp. 603-612.
Braidy, N., et al., "Effects of Kynurenine Pathway Metabolites on Intracellular NAD+ Synthesis and Cell Death in Human Primary Astrocytes and Neurons," International Journal of Tryptophan Research, 2009, vol. 2, pp. 61-69.
Medana, I.M., et al., "Metabolites of the Kynurenine Pathway of Tryptophan Metabolism in the Cerebrospinal Fluid of Malawian Children with Malaria," The Journal OfInfectious Diseases, 2003, vol. 188, p. 844-849.

* cited by examiner

TREATMENT OF BONE DISEASES

CROSS-REFERENCE TO RELATED APPLICATIONS

This application is a national phase application under 35 U.S.C. §371 of PCT International Application No. PCT/AU2012/001095, filed on 13 Sep. 2012, which claims priority from Australian Provisional Patent Application No. 2011903764 filed on 13 Sep. 2011, the entire contents of which are incorporated herein by cross-reference.

TECHNICAL FIELD

The invention relates generally to the field of bone diseases. More specifically, the invention relates to methods and compositions for the treatment of osteoporosis and related disorders.

BACKGROUND

Osteoporosis is a disease leading to excessive breakdown of bone substance and structure culminating in increased susceptibility to fracture. It is a common pathological condition in elderly people where it is associated with a high incidence of morbidity and pain, and in some cases permanent immobilization.

Osteoporotic bone breaks under minimal trauma and resulting fractures are difficult to treat. Bone fractures associated with osteoporosis occur mainly in the femoral neck, in the wrist, and in vertebrae. For example, vertebral compression fractures are common, the vast majority of which are associated with intense pain at the site of the fracture which may become chronic. Lung problems and loss of mobility are some general consequences of vertebral compression fractures and can be permanent in the elderly, often leading to death through secondary disorders (e.g. pneumonia or pulmonary embolism). There are approximately 20,000 hip fractures per year in Australians aged over 60 years (increasing by 40% each decade), and approximately 25% of those who sustain a hip fracture die within 12 months post-fracture (Osteoporosis Australia, (2007), "*The Burden of Brittle Bones*", White paper). Furthermore, of those who do not die following hip fracture, approximately 50% will suffer some level of dependence in their basic daily activities (such as toileting, grooming, etc.) representing a significant burden and health cost (Osteoporosis Australia (2007), "*The Burden of Brittle Bones*", White paper; Berry et al. (2007), "*Second hip fracture in older men and women: the Framingham Study*", Arch Intern Med.; 167:1971-6).

While the incidence of bone fracture in the elderly is generally increasing, therapeutic choices are limited. Currently, antiresorptives (e.g. bisphosphonates, denosumab, hormone therapy) are the most commonly used treatments for osteoporosis. These agents are designed to slow bone remodelling and increase bone density. However, they have been associated with significant side effects including osteonecrosis of the jaw, atypical fractures, atrial fibrillation, and increased risk of stroke or cancer. Anabolic agents may be used to generate new bone in patients with osteoporosis. However, finding anabolic factors that increase bone mass and regulate the balance between bone and fat has been challenging. In addition, the only commercially available anabolic agent (teriparatide) is not only very expensive and difficult to administer but is also associated with side effects including lowered blood pressure, nausea, pain, weakness, and depression. Moreover, the use of teriparatide in rats has been found to cause malignant tumour growth (osteogenic carcinoma). In general, therapeutic choices for osteoporosis are limited and the development of new therapeutic approaches that stimulate bone formation is a priority.

There is a need for alternative methods and compositions for the treatment of osteoporosis and related disorders.

SUMMARY OF THE INVENTION

The present inventors have identified certain compounds with osteogenic effects. The provision of these compounds to a subject in need thereof, for example, by direct administration or by manipulation of gene/protein expression in the subject, may be used to overcome one or more deficiencies of current treatments for osteoporosis and related disorders.

In a first aspect, the invention provides a method for inducing bone formation in a mammalian subject, the method comprising increasing cellular levels of a tryptophan-kynurenine pathway metabolite in the subject, wherein the metabolite is selected from the group consisting of picolinic acid and quinolinic acid.

In one embodiment of the first aspect, the method further comprises comparing the level of bone formation in said mammalian subject with the level of bone formation in a control subject or sample.

In a second aspect, the invention provides a method for preventing or treating a bone disease in a mammalian subject, the method comprising increasing cellular levels of a tryptophan-kynurenine pathway metabolite in the subject, wherein the metabolite is selected from the group consisting of picolinic acid and quinolinic acid.

In a third aspect, the invention provides a method for upregulating expression of an osteogenic gene in a mammalian subject, the method comprising increasing cellular levels of a tryptophan-kynurenine pathway metabolite in the subject, wherein the metabolite is selected from the group consisting of picolinic acid and quinolinic acid.

In one embodiment of the third aspect, the method further comprises comparing the level of expression of the osteogenic gene in cells of the subject with the level of expression of a corresponding osteogenic gene in control cells.

In one embodiment of the third aspect, the osteogenic gene is RUNX2, osteocalcin (OCN), osteopontin (OPN), or any combination thereof.

In a fourth aspect, the invention provides a method for inducing differentiation of a bone progenitor cell in a mammalian subject, the method comprising increasing cellular levels of a tryptophan-kynurenine pathway metabolite in the subject, wherein the metabolite is selected from the group consisting of picolinic acid and quinolinic acid.

In one embodiment of the fourth aspect, the bone progenitor cell is a mesenchymal stem cell.

In one embodiment of the fourth aspect, the method further comprises comparing the differentiation state of the bone progenitor cell with the differentiation state of a corresponding control bone progenitor cell.

In one embodiment of the above aspects, the increasing comprises administering a therapeutically effective amount of picolinic acid to the subject.

In one embodiment of the above aspects, the increasing comprises administering a therapeutically effective amount of quinolinic acid to the subject.

In one embodiment of the above aspects, the increasing comprises administering a therapeutically effective amount of quinolinic acid and picolinic acid to the subject.

In one embodiment of the above aspects, the increasing comprises administering to the subject a therapeutically effective amount of any one or more of N'-Formylkynurenine, L-Kynurenine, L-3-Hydroxykynurenine, 3-Hydroxyanthranilic acid, 2-Amino-3-carboxymuconic acid semialdehyde, or 2-Aminomuconic acid semialdehyde.

In one embodiment of the above aspects, the increasing comprises administering to the subject a therapeutically effective amount of any one or more of tryptophan 2,3-dioxygenase (EC 1.13.11.11), indoleamine 2,3-dioxygenase 1 (EC 1.13.11.52), kynurenine 3-monooxygenase (EC 1.14.13.9), 3-hydroxyanthranilate 3,4-dioxygenase (EC 1.13.11.6), or 2-amino-3-carboxymuconate-6-semialdehyde decarboxylase (EC 4.1.1.45).

In one embodiment of the above aspects, the increasing comprises administering a therapeutically effective amount of indoleamine 2,3-dioxygenase 1 (EC 1.13.11.52) to the subject.

In one embodiment of the above aspects, the increasing comprises increasing or decreasing the expression of a gene encoding a tryptophan-kynurenine pathway enzyme.

In one embodiment of the above aspects, the expression is increased and said gene encodes tryptophan 2,3-dioxygenase (EC 1.13.11.11), indoleamine 2,3-dioxygenase 1 (EC 1.13.11.52), kynurenine 3-monooxygenase (EC 1.14.13.9), 3-hydroxyanthranilate 3,4-dioxygenase (EC 1.13.11.6), or 2-amino-3-carboxymuconate-6-semialdehyde decarboxylase (EC 4.1.1.45).

In one embodiment of above aspects, the expression is decreased, and said gene encodes 2-aminoadipate aminotransferase (EC 2.6.1.39), alpha-aminoadipate aminotransferase (EC 2.6.1.7), or catalase (EC 1.11.1.6).

In one embodiment of above aspects, the method further comprises administering interferon gamma (IFNγ) to the subject.

In one embodiment of the second aspect, the bone disease is selected from the group consisting of osteoporosis; primary osteoporosis; secondary osteoporosis; osteogenesis imperfecta; osteodystrophy; osteopenia; Paget's disease; osteolytic lesions produced by bone metastasis, radiotherapy, or chemotherapy; periondontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures.

In one embodiment of the second aspect, the bone disease is osteoporosis.

In one embodiment of the above aspects, levels of the tryptophan-kynurenine pathway metabolite are increased in stem cells of the subject.

In one embodiment of the above aspects, levels of the tryptophan-kynurenine pathway metabolite are increased in mesenchymal stem cells of the subject.

In a fifth aspect, the invention provides use of an agent that increases cellular levels of a tryptophan-kynurenine pathway metabolite for the manufacture of a medicament for the prevention or treatment of a bone disease in a mammalian subject, wherein the metabolite is selected from the group consisting of picolinic acid and quinolinic acid.

In a sixth aspect, the invention provides an agent that increases cellular levels of a tryptophan-kynurenine pathway metabolite for use in the prevention or treatment of a bone disease in a mammalian subject, wherein the metabolite is selected from the group consisting of picolinic acid and quinolinic acid.

In one embodiment of the fifth and sixth aspect, the agent comprises any one or more of picolinic acid, quinolinic acid, indoleamine 2,3-dioxygenase 1 (EC 1.13.11.52), N'-Formylkynurenine, L-Kynurenine, L-3-Hydroxykynurenine, 3-Hydroxyanthranilic acid, 2-Amino-3-carboxymuconic acid semialdehyde, or 2-Aminomuconic acid semialdehyde, tryptophan 2,3-dioxygenase (EC 1.13.11.11), kynurenine 3-monooxygenase (EC 1.14.13.9), 3-hydroxyanthranilate 3,4-dioxygenase (EC 1.13.11.6), and/or 2-amino-3-carboxymuconate-6-semialdehyde decarboxylase (EC 4.1.1.45).

In one embodiment of the fifth and sixth aspect, the agent is capable of increasing or decreasing the expression of a gene encoding a tryptophan-kynurenine pathway enzyme.

In one embodiment of the fifth and sixth aspect, the agent is capable of increasing the expression of the gene, and the gene encodes tryptophan 2,3-dioxygenase (EC 1.13.11.11), indoleamine 2,3-dioxygenase 1 (EC 1.13.11.52), kynurenine 3-monooxygenase (EC 1.14.13.9), 3-hydroxyanthranilate 3,4-dioxygenase (EC 1.13.11.6), or 2-amino-3-carboxymuconate-6-semialdehyde decarboxylase (EC 4.1.1.45).

In one embodiment of the fifth and sixth aspect, the agent is capable of decreasing the expression of the gene, and the gene encodes 2-aminoadipate aminotransferase (EC 2.6.1.39), alpha-aminoadipate aminotransferase (EC 2.6.1.7), or catalase (EC 1.11.1.6).

In one embodiment of the fifth and sixth aspect, the agent comprises picolinic acid.

In one embodiment of the fifth and sixth aspect, the agent comprises quinolinic acid.

In one embodiment of the fifth and sixth aspect, the agent comprises quinolinic acid and picolinic acid.

In one embodiment of the fifth and sixth aspect, the agent comprises indoleamine 2,3-dioxygenase 1 (EC 1.13.11.52).

In one embodiment of the fifth and sixth aspect, the agent further comprises interferon gamma (IFNγ).

In one embodiment of the fifth and sixth aspect, the agent is capable of increasing levels of the tryptophan-kynurenine pathway metabolite in stem cells of the subject.

In one embodiment of the fifth and sixth aspect, the agent is capable of increasing levels of the tryptophan-kynurenine pathway metabolite in mesenchymal stem cells of the subject.

In one embodiment of the fifth and sixth aspect, the bone disease is selected from the group consisting of osteoporosis; primary osteoporosis; secondary osteoporosis; osteogenesis imperfecta; osteodystrophy; osteopenia; Paget's disease; osteolytic lesions produced by bone metastasis, radiotherapy, or chemotherapy; periondontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures.

In one embodiment of the fifth and sixth aspect, the bone disease is osteoporosis.

In a seventh aspect, the invention provides a composition for treating a bone disease in a mammalian subject comprising any one or more of picolinic acid, quinolinic acid, and/or indoleamine 2,3-dioxygenase 1 (EC 1.13.11.52).

In one embodiment of the seventh aspect, the composition comprises any two or more of picolinic acid, quinolinic acid, and/or indoleamine 2,3-dioxygenase 1 (EC 1.13.11.52).

In one embodiment of the seventh aspect, the composition comprises picolinic acid and quinolinic acid.

In one embodiment of the seventh aspect, the composition comprises picolinic acid, quinolinic acid and indoleamine 2,3-dioxygenase 1 (EC 1.13.11.52).

In one embodiment of the seventh aspect, the composition further comprises a pharmaceutically acceptable carrier, excipient or diluent.

In one embodiment of the seventh aspect, the composition further comprises interferon gamma (IFNγ).

In an eighth aspect, the invention provides use of the composition according to the seventh aspect for the treatment of a bone disease in a mammalian subject, wherein the bone disease is selected from the group consisting of osteoporosis; primary osteoporosis; secondary osteoporosis; osteogenesis imperfecta; osteodystrophy; osteopenia; Paget's disease; osteolytic lesions produced by bone metastasis, radiotherapy, or chemotherapy; periondontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures.

In one embodiment of the eighth aspect, the bone disease is osteoporosis.

In one embodiment of the above aspects, the mammalian subject is a human.

Figure 1:
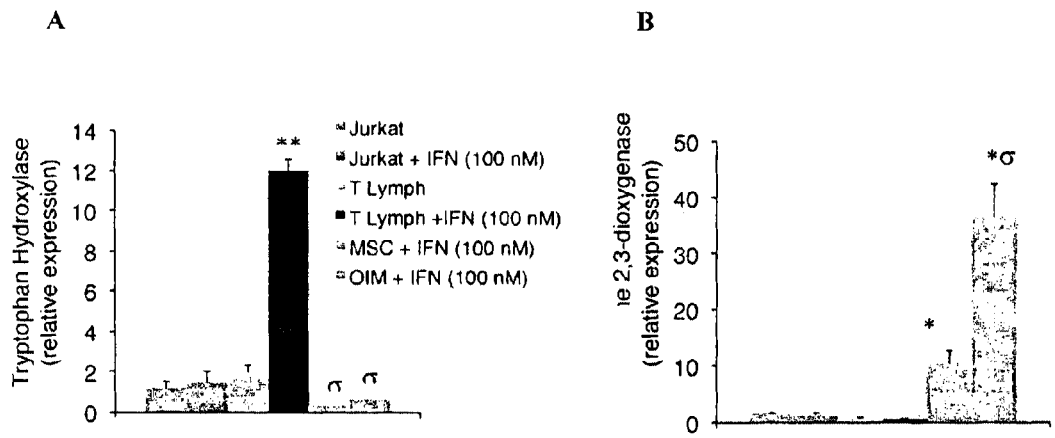
FIG. 1 provides two graphs showing changes in relative gene expression in IFNγ-treated (100 ng/ml for 7 days) Jurkat cells, human T-lymphocytes and MSC compared with untreated controls (mesenchymal stem cells (MSC) and immune cells) and quantified using real time PCR. (A) tryptophan hydroxylase (relative expression). (B) Indoleamine 2,3-dioxygenase (relative expression). Column 1: Jurkat cells; Column 2: Jurkat cells+IFNγ (100 nM); Column 3: T lymphocytes; Column 4: T lymphocytes+IFNγ (100 nM); Column 5: MSC+IFNγ (100 nM); osteoblastogenesis induction media (OIM)+IFNγ (100 nM). *$p<0.01$ treated vs. untreated MSC; σ $p<0.01$ treated MSC vs. treated immune cells; **$p<0.01$ treated vs. untreated T lymphocytes.

transcription after correction with housekeeping gene (GAPDH). (B) and (D): effect of PA on Runx2 (B) and OCN translation (D) measured by western blot. *p<0.01 treated vs. control mice within their corresponding group; σ p<0.01 OVX vs. their corresponding dose group of Sham operated mice.

DEFINITIONS

As used in this application, the singular form "a", "an" and "the" include plural references unless the context clearly dictates otherwise. For example, reference to "a metabolite" also includes a plurality of metabolites.

As used herein, the term "comprising" means "including". Variations of the word "comprising", such as "comprise" and "comprises," have correspondingly varied meanings. Thus, for example, a composition "comprising" metabolite A may consist exclusively of metabolite A, or, may include metabolite A and one or more additional components (e.g. metabolite B and/or metabolite C).

The term "therapeutically effective amount" as used herein, includes within its meaning a non-toxic but sufficient amount of a compound or composition for use in the invention to provide the desired therapeutic effect. The exact amount required will vary from subject to subject depending on factors such as the species being treated, the age and general condition of the subject, the severity of the condition being treated, the particular agent being administered, the mode of administration and so forth. Thus, it is not possible to specify an exact "effective amount". However, for any given case, an appropriate "effective amount" may be determined by one of ordinary skill in the art using only routine experimentation.

As used herein, the term "bone disease" refers to a disorder or condition associated with abnormality of the bone that can be treated by increasing bone mass and/or bone growth.

As used herein, the term "tryptophan-kynurenine pathway" is a reference a biochemical pathway of tryptophan metabolism in mammals commencing with the catabolism of tryptophan by either tryptophan 2,3-dioxygenase or indoleamine 2,3-dioxygenase, and terminating in the production of one or more of kynurenic acid (4-hydroxy-2-Quinolinecarboxylic acid), anthranilic acid (2-amino-4-(2-aminophenyl)-4-oxo-butanoic acid), xanthurenic acid (4,8-dihydroxy-quinoline-2-carboxylic acid), cinnavalininic acid (2-amino-3-oxo-phenoxazine-1,9-dicarboxylic acid), quinolinic acid (2,3-Pyridinedicarboxylic acid) or picolinic acid (pyridine-2-carboxylic acid).

As used herein, a "tryptophan-kynurenine pathway metabolite" encompasses all metabolites produced by the tryptophan-kynurenine pathway.

As used herein, a "tryptophan-kynurenine pathway enzyme" encompasses all enzymes that catalyse a reaction of the tryptophan-kynurenine pathway.

As used herein, the term "subject" includes any animal of economic, social or research importance including bovine, equine, ovine, primate, avian and rodent species. Hence, a "subject" may be a mammalian subject such as, for example, a human or a non-human mammal.

As used herein, the terms "antibody" and "antibodies" include IgG (including IgG1; IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein, the terms "protein" and "enzyme" will be understood to include analogues thereof. A protein or enzyme "analogue" is a derivative of the protein or enzyme, which derivative comprises addition, deletion, substitution of one or more amino acids, such that the protein or enzyme retains substantially the same function.

As used herein, the term "nucleic acid sequence" encompasses any single- or double-stranded polymer of deoxyribonucleotide or ribonucleotide bases, or known analogues or natural nucleotides, or mixtures thereof.

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing the assay etc.) from one location to another. For example, kits include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that each contains a subportion of the total kit components. The containers may be delivered to the intended recipient together or separately. Indeed, any delivery system comprising two or more separate containers that each contains a subportion of the total kit components are included in the term "fragmented kit".

As used herein, the term "combined kit" refers to a delivery system containing all of the components of a reaction assay in a single container (e.g. in a single box housing each of the desired components).

It will be understood that use the term "about" herein in reference to a recited numerical value includes the recited numerical value and numerical values within plus or minus ten percent of the recited value.

It will be understood that use of the term "between" herein when referring to a range of numerical values encompasses the numerical values at each endpoint of the range. For example, a nucleic acid sequence of between 10 base pairs and 20 base pairs in length is inclusive of a nucleic acid sequence of 10 base pairs in length and a nucleic acid sequence of 20 base pairs in length.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

DETAILED DESCRIPTION

The present invention relates to new methods and compositions for the treatment of osteoporosis and related disorders. In particular, the present inventors have unexpectedly identified that certain tryptophan metabolites have osteogenic properties making them suitable for treatment of osteoporosis and other related disorders where the generation of new bone is desirable.

Tryptophan is an essential amino acid metabolized through two primary pathways, namely, the tryptophan-kynurenine pathway and the tryptophan-serotonin pathway. Yadav et al (Yadav et al. (2010), "*Pharmacological inhibition of gut-derived serotonin synthesis is a potential bone anabolic treatment for osteoporosis*", Nat Med.; 16:308-12) have proposed a role of serotonin regulation in osteoporosis by treating oophorectomised (OVX) mice with LP533401, an inhibitor of gut-derived serotonin (GDS). The authors report that pharmacological inhibition of GDS stimulates bone formation and recues OVX mice from osteoporosis. The mechanism proposed by the authors is that serotonin exerts an inhibitory effect on gut production of lipoprotein receptor peptide 5 (LRP5) a potent stimulator of the Wnt/β-catenin pathway and thus of osteoblastogenesis. The approach suggested by the authors thus involves the inhibition of tryptophan metabolism to GDS. The prior art therefore indicates that inhibiting tryptophan metabolism to serotonin via the tryptophan-serotonin pathway provides a means of increasing osteogenesis.

In contrast, the present inventors have unexpectedly identified that increasing metabolism of tryptophan via the kynurenine pathway can be used to induce osteogenesis. More specifically, it has been identified that metabolites of tryptophan generated in the kynurenine pathway may be used to increase osteogenesis. Accordingly, in contrast to the prior art the present invention relates to the finding that increasing tryptophan metabolism via the tryptophan-kynurenine pathway is beneficial for osteogenesis.

There are also several notable risks inherent to the inhibition of GDS secretion as taught in the prior art, which are mostly explained by the physiologic role of GDS. For example, it would be expected that GDS inhibition is associated with alterations in gut motility, the most important function of GDS in the gut (see Sikander et al. (2009), "*Role of serotonin in gastrointestinal motility and irritable bowel syndrome*", Clin Chim Acta.; 403:47-55). These side effects are an important limitation in clinical practice. In contrast to LP533401 which inhibits an enzyme that is required in several biological functions including gut motility, the present invention avoids undesirable side effects by treatment with metabolites of the tryptophan-kynurenine pathway. The presently disclosed methods avoid the disadvantages of the prior art because instead of inhibiting a biologically required enzyme, end products of the kynurenine pathway are used without affecting the enzyme, which could be required for other unknown physiological processes. Further, tolerability is much improved as compounds of the present invention are vitamin-like and water soluble, which facilitates their pharmacokinetics and pharmacodynamics. Certain aspects of the present invention relate to compounds for stimulating osteogenesis. Compositions, kits and medicaments comprising compounds of the present invention are also provided. In certain embodiments, the compounds are kynurenine pathway tryptophan metabolites. In other embodiments, the compounds are capable of enhancing the production of kynurenine pathway tryptophan metabolites.

Other aspects of the present invention relate to methods for treating bone diseases (e.g. osteoporosis and related disorders). In certain embodiments, the methods comprise administering a compound, composition, or medicament of the present invention to a subject. In other embodiments, the methods comprise enhancing the expression of a gene and/or a protein (e.g. a kynurenine pathway enzyme or metabolite, or a gene encoding the same) in a subject.

Although the compounds and methods of the present invention are particularly suited to the treatment of osteoporosis, the skilled addressee will recognise that suitability exists for other applications where osteogenic effects are desirable.

Tryptophan-Kynurenine Pathway

In accordance with the present invention, osteogenesis may be enhanced in subject by the provision by one or more metabolites of the tryptophan-kynurenine pathway.

As known to those skilled in the art, the tryptophan-kynurenine pathway facilitates the conversion of tryptophan to niacin via a series of intermediates. Without being bound by theory, the pathway may commence with the conversion of tryptophan to N'-Formylkynurenine by tryptophan 2,3-dioxygenase or indoleamine-pyrrole 2,3-dioxygenase (IDO-1). N'-Formylkynurenine can be converted to L-kynurenine (kynurenine) by IDO-1. Kynurenine may undergo deamination in a standard transamination reaction yielding kynurenic acid. Alternatively, kynurenine may undergo a series of catabolic reactions producing 3-hydroxyanthranilate plus alanine. In this reaction series, kynureninase may catabolise the conversion of kynurenine into anthranilic acid while kynurenine-oxoglutarate transaminase (also known as Kynurenine amino-transferase and glutamine transaminase K, GTK) may catabolise its conversion into kynurenic acid and kynurenine 3-hydroxylase- to 3-hydroxykynurenine. The oxidation of 3-hydroxyanthranilate may convert it into 2-amino-3-carboxymuconic 6-semialdehyde which may in turn be converted to picolinic acid and quinolinic acid (a precursor of NAD). Quinolinic acid may be converted to nicotinic acid mononucleotide (NaMN) by transfer of a phosphoribose group. An adenylate group may then be transferred to form nicotinic acid adenine dinucleotide (NaAD), and the nicotinic acid group in NaAD amidated to a nicotinamide (Nam) group, forming nicotinamide adenine dinucleotide. In a further step, NAD+ may be converted into NADP+ by NAD+ kinase, which phosphorylases NAD+.

Picolinic and Quinolinic Acid Production

The present inventors have identified that at least two metabolites of the tryptophan-kynurenine pathway, picolinic acid (pyridine-2-carboxylic acid) and quinolinic acid (2,3-Pyridinedicarboxylic acid), have osteogenic properties. Accordingly, increasing the level of either or both of these metabolites in a subject provides a means of enhancing osteogenesis in the subject.

In accordance with the present invention, picolinic acid and/or quinolinic acid may be generated by any means known in the art. Apart from standard commercial sources (e.g. Sigma chemical company), the compounds may be synthesised artificially using a number of standard techniques. For example, picolinic acid may be produced using methods described in U.S. Pat. No. 4,666,841 issued to Hagedorn on 19 May 1987 and U.S. Pat. No. 4,859,592 issued to Hagedorn et al. on 22 Aug. 1989. Quinolinic acid may be produced, for example, using methods described in Alchmerova et al. (2001), "*Methods of preparation of quinolinic acid*", Bashkirskii Khimicheskii Zhurnal: 8(2), 9-14; U.S. Pat. No. 4,736,036 issued to Mathiaparanam on 5 Apr. 1988; or U.S. Pat. No. 4,537,971 issued to Rebhahn, et al. on 27 Aug. 1985).

Additionally or alternatively, picolinic acid and/or quinolinic acid may be generated by increasing the production of either or both compounds within an individual. For example, picolinic acid and/or quinolinic acid may be increased in an individual by manipulation of the tryptophan-kynurenine pathway.

The skilled addressee will recognise that the tryptophan-kynurenine pathway involves a number of different stages and subpathways with a potential to be manipulated to achieve increased production of picolinic acid and/or quinolinic acid.

For example, the production of picolinic acid and/or quinolinic acid in an individual may be increased by increasing the level of one or more metabolites in the tryptophan-kynurenine pathway from which picolinic acid and/or quinolinic acid are directly or indirectly derived. Non-limiting examples of such metabolites include: N'-Formylkynurenine (2-amino-4-(2-formamidophenyl)-4-oxo-butanoic acid); L-Kynurenine (2-amino-4-(2-aminophenyl)-4-oxo-butanoic acid); L-3-Hydroxykynurenine ((2S)-2-amino-4-(2-amino-3-hydroxyphenyl)-4-oxobutanoic acid); 3-Hydroxyanthranilic acid (2-amino-3-hydroxy-benzoic acid); 2-Amino-3-carboxymuconic acid semialdehyde (2-amino-3-(3-oxoprop-1-enyl)but-2-enedioic acid); 2-Aminomuconic acid semialdehyde (2-amino-6-oxo-hexa-2,4-dienoic acid); Picolinic acid (pyridine-2-carboxylic acid); Quinolinic acid (2,3-Pyridinedicarboxylic acid); and any combination of the aforementioned metabolites. In certain embodiments, the metabolite is picolinic acid and/or quinolinic acid. It will be understood that increasing the level of one or more metabolites in the tryptophan-kynurenine pathway may be achieved by any means including, for example, administering the metabolites, or otherwise manipulating the tryptophan-kynurenine pathway within the subject.

Additionally or alternatively, the production of picolinic acid and/or quinolinic acid in an individual may be increased by increasing or decreasing the expression and/or activity of one or more enzymes and/or enzyme cofactors of the tryptophan-kynurenine pathway. For example, the production of picolinic acid and/or quinolinic acid may be increased by increasing the expression and/or activity of one or more enzymes and/or cofactors affecting the production of a metabolite in the tryptophan-kynurenine pathway. Non-limiting examples of such enzymes include Tryptophan 2,3-dioxygenase (EC 1.13.11.11); Indoleamine 2,3-dioxygenase 1 (EC 1.13.11.52); Kynurenine 3-monooxygenase (EC 1.14.13.9); 3-hydroxyanthranilate 3,4-dioxygenase (EC 1.13.11.6); 2-amino-3-carboxymuconate-6-semialdehyde decarboxylase (EC 4.1.1.45); and any combination of the aforementioned enzymes. In certain embodiments, the enzyme is Indoleamine 2,3-dioxygenase 1 (EC 1.13.11.52). In certain embodiments, the enzyme is Indoleamine 2,3-dioxygenase 1 (EC 1.13.11.52) and the expression and/or activity is increased by administering IFNγ.

Additionally or alternatively, the production of picolinic acid and/or quinolinic acid may be increased by decreasing the expression and/or activity of one or more enzymes and/or cofactors affecting the production of a metabolite in the tryptophan-kynurenine pathway. Non-limiting examples of such enzymes include 2-aminoadipate aminotransferase (EC 2.6.1.39); Alpha-aminoadipate aminotransferase (EC 2.6.1.7); Catalase (EC 1.11.1.6); and any combination of the aforementioned enzymes.

It will be understood that increasing or decreasing the expression and/or activity of one or more enzymes and/or cofactors affecting the production of a metabolite in the tryptophan-kynurenine pathway may be achieved by any means including, for example, administering the enzymes, or otherwise manipulating the tryptophan-kynurenine pathway within the subject.

Additionally or alternatively, cellular levels of picolinic acid and/or quinolinic acid in an individual may be increased by inhibiting or preventing the metabolism of these compounds. For example, the production or activity of nicotinate-nucleotide pyrophosphorylase (EC 2.4.2.19) (also known as quinolinate phosphoribosyl transferase) may be inhibited to inhibit or prevent the further metabolism of quinolinic acid. Additionally or alternatively, the level of picolinic acid may be increased by inhibiting or preventing the production or activity of an enzyme that catalyses the metabolism of picolinic acid to another compound.

Additionally or alternatively, the level of quinolinic acid may be increased by inhibiting the production of picolinic acid. For example, the enzyme picolinate carboxylase may be inhibited by an increase in aminocarboxymuconic semialdehyde concentration, thereby instigating an increase in quinolinic acid levels.

Additionally or alternatively, the level of picolinic acid may be increased by inhibiting the production of quinolinic acid. For example, the non-enzymic cyclisation of aminocarboxymuconic semialdehyde to quinolinic acid may be inhibited or reduced using a suitable agent and/or by increasing the levels of metabolites derived from metabolising quinolinic acid.

The production of picolinic acid and/or quinolinic acid in a subject may be increased by increasing the level of one or more metabolites in the tryptophan-kynurenine pathway, and increasing or decreasing the expression and/or activity of one or more enzymes and/or cofactors in the tryptophan-kynurenine pathway.

In certain embodiments, the production of quinolinic acid and picolinic acid in a subject may be increased by administering quinolinic acid and picolinic acid in combination. The quinolinic acid and picolinic acid may be administered in combination with interferon gamma (IFNγ).

In some embodiments, the production of picolinic acid in a subject may be increased by administering picolinic acid and increasing the expression and/or activity of indoleamine 2,3-dioxygenase 1. The expression and/or activity of indoleamine 2,3-dioxygenase 1 may be increased by administering IFNγ.

In other embodiments, the production of quinolinic acid in a subject may be increased by administering quinolinic acid and increasing the expression and/or activity of indoleamine 2,3-dioxygenase 1. The expression and/or activity of indoleamine 2,3-dioxygenase 1 may be increased by administering IFNγ.

In further embodiments, the production of quinolinic acid and picolinic acid in a subject may be increased by administering quinolinic acid and picolinic acid, and increasing the expression and/or activity of indoleamine 2,3-dioxygenase 1. The expression and/or activity of indoleamine 2,3-dioxygenase 1 may be increased by administering IFNγ.

It will be understood that reference to "increasing" the production, level or activity of a given metabolite or enzyme in a subject means elevating the production, level or activity of the metabolite or enzyme above that which exists prior to intervention in accordance with the present invention. Reference to "decreasing", "inhibiting" or "reducing" the production, level or activity of the metabolite or enzyme means diminishing the production, level or activity of the metabolite or enzyme in a subject below that which exists prior to intervention in accordance with the present invention. For example, a change in the production, level or activity of a given metabolite or enzyme can readily be determined by determining the production, level or activity of the metabolite or enzyme in a subject under standard/ordinary biological conditions. This can be compared with the production, level or activity of the metabolite or enzyme after administering an agent or compound intended to have a desired effect.

The production, level or activity of the metabolite or enzyme in a subject under standard/ordinary biological conditions may be determined from a series of measurements taken over different timepoints to provide a standard range. Additionally or alternatively, the production, level or activity of the metabolite or enzyme may be measured in multiple individuals to provide a standard range representative of a given population. In certain embodiments, the production, level or activity the metabolite or enzyme may be increased or reduced by at least about 2%, at least about 3%, at least about 4%, at least about 5%, at least about 10%, at least about 15%, at least about 20%, at least about 30%, at least about 40%, at least about 50%, at least about 60%, at least about 70%, or at least about 80%, compared to its production, level or activity under standard/ordinary biological conditions.

Metabolites of the tryptophan-kynurenine pathway can be detected and quantified using standard techniques known in the art including, for example, high-performance liquid chromatography (HPLC), gas chromatography-mass spectrometry (GC-MS), electron-capture negative ion mass spectrometry and the like (see, for example, techniques described in Medana et al. (2002), *"The clinical significance of cerebrospinal fluid levels of kynurenine pathway metabolites and lactate in severe malaria"*, J Infect Dis; 185(5):650-6; Medana et al. (2003), *"Metabolites of the kynurenine pathway of tryptophan metabolism in the cerebrospinal fluid of Malawian children with malaria"*, J Infect Dis.:188(6):844-9; Dazzi et at (2001), *"High-performance liquid chromatographic method for the detection of picolinic acid in biological fluids"*, J Chromatogr B Biomed Sci Appl. 10:751 (1):61-8; Liebich and Forst (1990), *"Basic profiles of organic acids in urine"*, J Chromatogr. 26:525(1):1-14; Smythe et al. (2003), *"ECNI GC-MS analysis of picolinic and quinolinic acids and their amides in human plasma, CSF, and brain tissue"*, Adv Exp Med Biol.: 527:705-12; and Moroni et al. (1986), *"Increase in the content of quinolinic acid in cerebrospinal fluid and frontal cortex of patients with hepatic failure.* J Neurochem.:47(6):1667-71).

Osteogenic Treatments

As noted in the sections above, the present invention provides tryptophan metabolites with osteogenic properties making them suitable for treatment of osteoporosis and other related disorders where the generation of new bone is desirable.

Accordingly, the present invention provides methods and compositions for the prevention and/or treatment of osteoporosis and related disorders. In general, the methods comprise increasing cellular levels of one or more tryptophan-kynurenine pathway metabolites having osteogenic properties in a subject. Without limitation to theory, the osteogenic effect may be induced by stimulating the osteogenic properties of the cells and/or inhibiting their adipogenic or bone resorbing properties. For example, cellular levels of one or more tryptophan-kynurenine pathway metabolites may be increased in bone cells (e.g. osteoblasts, osteocytes, osteoclasts, or bone progenitor cells) and/or stem cells (e.g. mesenchymal stem cells) of the subject. In addition, cellular levels of one or more tryptophan-kynurenine pathway metabolites may be increased in fat cells (adipocytes) and/or osteoclasts of the subject in order to induce their transdifferentiation into bone (in the case of the adipocytes) and/or inhibit their bone resorbing activity (in the case of osteoclasts).

In some embodiments, the methods of the present invention comprise increasing the expression of osteogenic genes in a mammalian subject. Non-limiting examples of these osteogenic genes include RUNX2, osteocalcin (OCN), osteopontin (OPN), or any combination thereof.

The methods of the present invention may be used for inducing differentiation of bone progenitor cells in a mammalian subject. For example, the methods may be used to induce differentiation of stem cells (e.g. mesenchymal stem cells) into bone cells.

In certain embodiments, the methods comprise administering a composition of the present invention or a medicament of the present invention. Non-limiting examples of suitable compositions and medicaments are provided in the section below entitled "Compositions, medicaments, dosages and routes of administration".

Methods of prevention and/or treatment according to the present invention may comprise administering one or more metabolites and/or enzymes of the tryptophan-kynurenine pathway. Non-limiting examples of suitable metabolites and enzymes are provided in the section above entitled "Picolinic and quinolinic acid production".

For example, methods of prevention and/or treatment according to the present invention may comprise administering any one or more of quinolinic acid, picolinic acid, indoleamine 2,3-dioxygenase 1, and/or IFNγ to the subject.

Suitable dosages of these compounds may be calculated using appropriate systems as known in the art without requiring inventive effort.

For example, the HED system may be used which is based on body weight as follows:

$$HED = \text{animal } NOAEL \times (W_{animal}/W_{human})^{(1-b)}$$

The calculated dosage for humans (based on mouse experiments) may be:
quinolinic acid: about 200 mg/m$^2$;
picolinic acid: about 100 mg/m$^2$;
IFNγ: 0.5 micrograms per kilogram, three times per week. This dose has been calculated based on the already approved dosing in humans suffering of osteopetrosis, adjusted according to our recent publication on the osteogenic dose of IFNγ in mice (Duque et al. (2011), *"Interferon-γ plays a role in bone formation in vivo and rescues osteoporosis in ovariectomized mice"*, J Bone Miner Res. 2011 July; 26(7):1472-83).

In some embodiments, the methods comprise administering quinolinic acid. In some embodiments, the methods comprise administering picolinic acid. In other embodiments, the methods comprise administering quinolinic acid and picolinic acid.

In additional embodiments, the methods comprise administering quinolinic acid and/or picolinic acid, and indoleamine 2,3-dioxygenase 1.

In embodiments where multiple metabolites and/or enzymes are administered, the individual components of the treatment may be administered simultaneously or sequentially.

Methods of prevention and/or treatment according to the present invention may comprise administering one or more agents capable of altering the expression of at least one gene encoding an enzyme of the tryptophan-kynurenine pathway. Non-limiting examples of suitable enzymes encoded by the genes are provided in the section above entitled "Picolinic and quinolinic acid production". Altering expression of the gene or genes may serve to increase cellular levels of one or more metabolites of the tryptophan-kynurenine pathway (e.g. quinolinic acid and/or picolinic acid).

In certain embodiments, the methods comprise enhancing the expression of one or more genes encoding an enzyme of the tryptophan-kynurenine pathway. This may be used as a means for increasing cellular levels of the encoded enzyme (s) which may in turn increase cellular levels of one or more metabolites of the tryptophan-kynurenine pathway. Preferably, at least one of said metabolites is quinolinic acid or picolinic acid. More preferably, cellular levels of both quinolinic acid and picolinic acid are increased. The gene may encode tryptophan 2,3-dioxygenase, indoleamine 2,3-dioxygenase 1, kynurenine 3-monooxygenase, 3-hydroxyanthranilate 3,4-dioxygenase, or 2-amino-3-carboxymuconate-6-semialdehyde decarboxylase. In some preferred embodiments, the gen encodes indoleamine 2,3-dioxygenase 1.

Additionally or alternatively, the methods may comprise inhibiting the function or activity of an enzyme of the tryptophan-kynurenine pathway (e.g. by administering an antagonist of the enzyme such as, for example, an antibody specific for the enzyme), or, increasing the function or activity of an enzyme of the tryptophan-kynurenine pathway (e.g. by administering an agonist of the enzyme such as, for example, a cofactor for the enzyme).

In certain embodiments, the methods comprise reducing the expression of one or more genes encoding an enzyme of the tryptophan-kynurenine pathway. This may be used as a means of decreasing cellular levels of the encoded enzyme (s) which may in turn increase cellular levels of one or more metabolites of the tryptophan-kynurenine pathway. Preferably, at least one of said metabolites is quinolinic acid or picolinic acid. More preferably, cellular levels of both quinolinic acid and picolinic acid are increased. The genes may encode 2-aminoadipate aminotransferase, alpha-aminoadipate aminotransferase, or catalase.

Any suitable method to increase the expression of a target gene in a subject may be utilised.

For example, the expression of a gene may be increased in the cells of a subject using various methods of gene delivery known in the art. For example, an expression vector (e.g. a plasmid vector) comprising a nucleic acid sequence (e.g. DNA, cDNA or RNA) encoding a tryptophan-kynurenine pathway enzyme operably linked to an expression control sequence such as an inducible promoter may be administered to a subject to increase cellular production of the enzyme. Typically the vector may include expression control and processing sequences such as a promoter, an enhancer, ribosome binding sites, polyadenylation signals and transcription termination sequences. Alternatively, viral vectors (for example retroviral and adenoviral vectors) containing the nucleic acid sequence may be administered to a subject to increase cellular production of the enzyme. The delivery of the nucleic acid may also be achieved by extracting cells from a subject, administering a vector containing the nucleic acid of interest, and then re-introducing the cells to the subject. The vector may comprise naked DNA or may be in the form of a composition, together with one or more pharmaceutically acceptable carriers.

Any suitable method to decrease the expression of a target gene in a subject may be utilised.

For example, the expression of a gene may be decreased in the cells of a subject using various methods including antisense oligonucleotides, small interfering RNA (siRNA) sequences, and/or ribozymes (e.g. hammerhead or hairpin ribozymes).

Methods for the design, synthesis, and delivery of antisense nucleic acids are well known in the art. The antisense molecules may be DNA or RNA, or partial or complete synthetic analogues thereof. Antisense constructs (e.g. 10-30 base pairs in length) may be generated which are at least substantially complementary along their length to a region of the gene in question. Binding of an antisense construct to its complementary cellular sequence may interfere with transcription, RNA processing, transport, translation and/or mRNA stability.

Small interfering RNA (siRNA) sequences are small, usually double-stranded RNA oligonucleotides, for example at 21, 27 or 29 bases in length with or without overhangs, which specifically hybridise with RNA sequences of interest and which serve as substrates for the RNA-induced silencing complex. Double-stranded RNA molecules may be synthesised in which one strand is identical to a specific region of the mRNA transcript to be silenced, and this double stranded RNA may be introduced directly. Alternatively, corresponding dsDNA can be employed, which, once presented intracellularly is converted into dsRNA. Methods for the synthesis of suitable siRNA molecules for use in RNA interference (RNAi) and for achieving post-transcriptional gene silencing are known to those of skill in the art, and commercial services exist for designing and producing siRNAs. siRNAs may be introduced into a cell by way of a vector, for example via a viral-mediated delivery mechanism such as an adeno-associated virus vector, or delivered exogenously, for example when delivered as part of a liposome complex. Techniques for the non-viral delivery of synthetic siRNAs in vivo are reviewed in Akhtar and Benter, (2007), J. Clin. Invest 117:3623-3632. Suitable techniques for the administration of siRNA sequences locally or systemically include those for mice (Yano et al, (2004), Clinical Cancer Research 10: 7721-7726), primates (Zimmermann et al, (2006), Nature 441(7089): 111-114) and humans (Nogawa et al. (2006), J Clin Invest 115:978-985), The use of siRNA delivery systems such as cholesterol-siRNA conjugates, cationic delivery systems, including cationic nanoparticles or cationic liposomes or cationic polymer or peptide delivery systems, or chitosan-siRNA conjugates, is contemplated.

Ribozymes, such as hammerhead or hairpin ribozymes, are capable of targeted catalytic cleavage and splicing of specific RNA sequences, including mRNA and genomic RNA sequences. The design and methods for the delivery of ribozymes are reviewed, for example, in Vaish et al, (1998), Nucleic Acids Research 26:5237-5242; Lieber and Strauss, (1995), Mol. Cell. Biol. 15:540-551; and Usman and Blatt, (2000), J Clin Invest 106:1197-1202.

As a practical matter, sequence identity between an antisense oligonucleotide, siRNA or ribozyme, and a target gene encoding an enzyme of the tryptophan-kynurenine pathway can be determined conventionally using known computer programs such as the Bestfit program (Wisconsin Sequence Analysis Package, Version 8 for Unix, Genetics Computer Group, University Research Park, 575 Science Drive, Madison, Wis. 53711).

Methods of prevention and/or treatment according to the present invention can be used to increase osteogenesis in a subject.

It will be understood that reference to "increasing" osteogenesis, osteogenic gene expression, or bone cell progenitor differentiation in a subject means elevating the level of osteogenesis, osteogenic gene expression, or bone cell progenitor differentiation above that which exists prior to treatment in accordance with the present invention. For example, a change in the level can readily be determined by comparing levels in a subject before and after treatment. The level of osteogenesis, osteogenic gene expression, or bone cell progenitor differentiation before and/or after treatment may be determined from a series of measurements taken over different timepoints to provide a standard range. The level of osteogenesis osteogenic gene expression, or bone cell progenitor differentiation before and/or after treatment may be measured in multiple individuals to provide a standard range representative of a given population. In certain embodiments, the level of osteogenesis, osteogenic gene expression, or bone cell progenitor differentiation may be increased in a subject treated by the methods of the present invention by at least about 2%, at least about 3%, at least about 4%, at least about 5%, at least about 10%, at least about 15%, at least about 20%, at least about 30%, at least about 40%, at least about 50%, at least about 60%, at least about 70%, or at least about 80%, compared to the level of osteogenesis, osteogenic gene expression, or bone cell progenitor differentiation prior to treatment.

The efficacy of methods for preventing or treating diseases provided herein may be determined using any suitable technique for quantifying the level of osteogenesis. Commercial kits for quantifying the level of osteogenesis are available (e.g. Millipore osteogenesis quantitation kit, Cat # ECM815). Additionally or alternatively, the level of osteogenesis can be determined by quantifying mRNA levels of genes associated with osteogenesis (e.g. RUNX2, OCN and OPN) using techniques such as RT-PCR, and/or other methods such as alkaline phosphatase assays, alizarin red-S and von Kossa staining, and the like.

The methods and compositions of the present invention may be used to increase osteogenesis and thus find particular application in the prevention and/or treatment of diseases where bone growth is affected.

As used herein, "bone disease" refers to a disorder or condition associated with abnormality of the bone that can be treated by increasing bone mass and/or bone growth.

Bone mass may be measured in mammalian subjects (e.g. humans) using standard techniques (e.g. dual energy X-ray absorptiometry (DXA)). In particular, DXA may be used for diagnosis, prognosis (e.g. fracture prediction), monitoring the progression of a bone disease, and/or assessing responses to treatment. Categorisation of subjects into diseased and non-diseased states based on bone mass (i.e. bone material density) can be made on the basis of standard classification systems including those published by the World Health Organisation (see, for example, World Health Organization Technical Report Series 921 (2003), Prevention and Management of Osteoporosis). For example, a diagnosis of osteoporosis may be based on BMD that is two standard deviations or more below a young adult reference mean.

Additionally or alternatively, a diagnosis of a given bone disease can be made by a physician, nurse, or veterinarian, depending on the subject under consideration.

Non-limiting examples of bone diseases that may be treated by the methods of the present invention include osteoporosis; primary osteoporosis; secondary osteoporosis; osteogenesis imperfecta; osteodystrophy; osteopenia; Paget's disease; osteolytic lesions produced by bone metastasis, radiotherapy, or chemotherapy; periondontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures.

In certain embodiments, the disease is osteoporosis.

In certain embodiments, the disease is secondary osteoporosis. The secondary osteoporosis may be associated with immobilization, or the use of a drug or medication.

The methods and compositions of the present invention may be used for any other application that derives benefit from increasing bone growth and/or bone mass including, but not limited to, increasing bone synostosis; enhancing long bone extension; enhancing prosthetic ingrowth; and enhancing bone healing following facial reconstruction, maxillary reconstruction, mandibular reconstruction, or tooth extraction.

Methods for treating bone diseases according to the present invention can be used in combination with other treatments (see, for example, Williams Textbook of Endocrinology, 10$^{th}$ Edition, Larsen et al. Eds. (2002), W.B. Saunders Company; World Health Organization Technical Report Series 921 (2003), "*Prevention and Management of Osteoporosis*"; and Endocrinology and Metabolism, 4$^{th}$ Edition, Felig et al. Eds. (2001), McGraw-Hill Book Company).

"Subjects" and "recipients" treated by the methods of the present invention include humans and individuals of any mammalian species of social, economic or research importance including, but not limited to, members of the genus ovine, bovine, equine, porcine, feline, canine, primates, and rodents.

Subjects and recipients treated by the methods of the present invention may be suffering from a bone disease, or suspected to be suffering from a bone disease. Alternatively, subjects treated may not be suffering from a bone disease but may be susceptible to suffering from a bone disease. A determination of whether a given subject is suffering from a given bone disease or is susceptible to a given bone disease can be made by those of skilled in the art based on clinical symptoms and/or other standard diagnostic tests which may vary depending on the particular disease in question.

The present invention provides methods for the production of medicaments for treating bone diseases.

In certain embodiments, the present invention provides the use of one or more agents that increase cellular levels of a tryptophan-kynurenine pathway metabolite in the manufacture of a medicament for the prevention or treatment of a bone disease in a subject. In other embodiments, the present invention provides one or more agents that increase cellular levels of a tryptophan-kynurenine pathway metabolite for use in the prevention or treatment of a bone disease in a subject.

The agent or agents may be a tryptophan-kynurenine pathway metabolite and/or enzyme (e.g. one or more of picolinic acid, quinolinic acid, and indoleamine 2,3-dioxygenase 1).

The agent or agents may increase or decrease the expression of one or more genes encoding an enzyme of the tryptophan-kynurenine pathway (e.g. a vector comprising a nucleic acid sequence of one or more of the genes, an antisense oligonucleotide or siRNA specific for one or more of the genes).

The agents may be administered simultaneously or sequentially.

Non-limiting examples of diseases that may be treated or prevented include osteoporosis; primary osteoporosis; secondary osteoporosis; osteogenesis imperfecta; osteodystrophy; osteopenia; Paget's disease; osteolytic lesions produced by bone metastasis, radiotherapy, or chemotherapy; periondontal disease; alveolar bone loss; bone loss due to immobilization or sex hormone deficiency; bone loss due to metastatic cancer; bone and cartilage loss caused by an inflammatory disease; osteoarthritis; osteotomy bone loss; childhood idiopathic bone loss; curvature of the spine; and bone fractures.

Compositions, Medicaments, Dosages and Routes of Administration

The present invention provides compositions and medicaments for increasing osteogenesis in subjects, and methods for producing the same. The compositions and medicaments may be used for the treatment of bone diseases such as osteoporosis and related disorders.

Compositions, medicaments and kits of the present invention may comprise at least one metabolite or enzyme of the tryptophan-kynurenine pathway. In certain embodiments, the metabolite or enzyme may be capable of increasing the production of picolinic acid and/or quinolinic acid in a subject to which it is administered. In other embodiments, the compositions and medicaments comprise picolinic acid and/or quinolinic acid.

Non-limiting examples of suitable metabolites that may be included in compositions and medicaments of the present invention include: N'-Formylkynurenine (2-amino-4-(2-formamidophenyl)-4-oxo-butanoic acid); L-Kynurenine (2-amino-4-(2-aminophenyl)-4-oxo-butanoic acid); L-3-Hydroxykynurenine ((2S)-2-amino-4-(2-amino-3-hydroxyphenyl)-4-oxobutanoic acid); 3-Hydroxyanthranilic acid (2-amino-3-hydroxy-benzoic acid); 2-Amino-3-carboxymuconic acid semialdehyde (2-amino-3-(3-oxoprop-1-enyl)but-2-enedioic acid); 2-Aminomuconic acid semialdehyde (2-amino-6-oxo-hexa-2,4-dienoic acid); Picolinic acid (pyridine-2-carboxylic acid); Quinolinic acid (2,3-Pyridinedicarboxylic acid); and any combination of the aforementioned metabolites.

Non-limiting examples of suitable enzymes that may be included in compositions and medicaments of the present invention include: Tryptophan 2,3-dioxygenase (EC 1.13.11.11); Indoleamine 2,3-dioxygenase 1 (EC 1.13.11.52); Kynurenine 3-monooxygenase (EC 1.14.13.9); 3-hydroxyanthranilate 3,4-dioxygenase (EC 1.13.11.6); 2-amino-3-carboxymuconate-6-semialdehyde decarboxylase (EC 4.1.1.45); and any combination of the aforementioned enzymes.

In certain embodiments, compositions, kits and medicaments of the present invention may comprise a combination of different tryptophan-kynurenine pathway metabolites. For example, the compositions or medicaments may comprise picolinic acid and quinolinic acid.

In other embodiments, compositions, kits and medicaments of the present invention may comprise a combination of different tryptophan-kynurenine pathway enzymes, or a combination of tryptophan-kynurenine pathway enzymes and metabolites. For example, the compositions, kits and medicaments may comprise picolinic acid and/or quinolinic acid in combination with Indoleamine 2,3-dioxygenase 1.

In still other embodiments, compositions, kits and medicaments of the present invention may comprise one or more tryptophan-kynurenine pathway metabolites and/or one or more tryptophan-kynurenine pathway enzymes in combination with IFNγ.

Kits of the present invention may comprise additional components to assist in conducting the methods of the invention such as, for example, buffers, diluents, saline solutions, means of administering components to an individual (e.g. a syringe) and/or instructions for use. Kits of the present invention may be fragmented kits or combined kits. The kits may comprise one or more compositions or medicaments of the present invention.

Compositions of the present invention may comprise a pharmaceutically acceptable carrier, adjuvant and/or diluent. The carriers, diluents and adjuvants must be "acceptable" in terms of being compatible with the other ingredients of the composition, and are generally not deleterious to the recipient thereof. Non-limiting examples of pharmaceutically acceptable carriers or diluents are demineralised or distilled water; saline solution; vegetable based oils such as peanut oil, safflower oil, olive oil, cottonseed oil, maize oil; sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from about 10% to about 99.9% by weight of the compositions.

Additionally or alternatively, compositions of the present invention may comprise an immunosuppressive agent, non-limiting examples of which include anti-inflammatory compounds, bronchodilatory compounds, cyclosporines, tacrolimus, sirolimus, mycophenolate mofetil, methotrexate, chromoglycalates, theophylline, leukotriene antagonist, and antihistamine, and combinations thereof. The immunosuppressive agent may also be an immunosuppressive drug or a specific antibody directed against B or T lymphocytes, or surface receptors that mediate their activation. For example, the immunosuppressive drug may be cyclosporine, tacrolimus, sirolimus, mycophenolate mofetil, methotrexate, chromoglycalates, theophylline, leukotriene antagonist, and antihistamine, or a combination thereof.

Additionally or alternatively, compositions of the present invention may comprise a steroid, such as a corticosteroid.

Compositions of the present invention may be in a form suitable for administration by injection, in a form of a formulation suitable for oral ingestion (such as capsules, tablets, caplets, elixirs, for example), in a form of an ointment, cream or lotion suitable for topical administration, in a form suitable for delivery as an eye drop, in an aerosol form suitable for administration by inhalation, such as by intranasal inhalation or oral inhalation, or in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl stearate which delay disintegration. Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono-or di-oleate, -stearate or-laurate, polyoxyethylene sorbitan mono-or di-oleate, -stearate or-laurate and the like.

Emulsions for oral administration may comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa.

Topical formulations of the present invention may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil, wool fat or its derivatives, or a fatty acid such as stearic or oleic acid together with an alcohol such as propylene glycol or macrogols.

Compositions of the present invention may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Compositions of the present invention may be administered in the form of a liposome. Liposomes are generally derived from phospholipids or other lipid substances, and are formed by mono-or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to Prescott, (Ed), (1976), "*Methods in Cell Biology*", Volume XIV, Academic Press, New York, N.Y. p. 33.

The therapeutically effective dose of a composition or medicament of the present invention for any given subject will depend upon a variety of factors including: the disease being treated and the severity/degree of progression of the disease; the subject's characteristics (e.g. age, body weight, general health, sex and diet of the subject); whether the compound is being used as single agent or in a combination therapy; the time of administration; the route of administration; the rate of sequestration of the composition or medicament; the duration of the treatment; the activity of the compound or agent employed; and other related factors known in the art.

Various general considerations that may be considered when determining an appropriate dosage of a composition or medicament of the present invention are described, for example, in Gennaro et al. (eds), (1990), "*Remington's Pharmaceutical Sciences*", Mack Publishing Co., Easton, Pa., USA; and Gilman et al., (eds), (1990), "*Goodman And Gilman's: The Pharmacological Bases of Therapeutics*", Pergamon Press.

Further, it will be apparent to one of ordinary skill in the art that the optimal quantity and spacing of individual dosages will be determined by the nature and extent of the disease being treated, the form, route and site of administration, and the nature of the particular subject being treated.

One skilled in the art would be able, by routine experimentation, to determine an effective, non-toxic amount of a composition or medicament of the present invention which would be required to effectively prevent or treat an applicable disease.

For example, an optimal dosage may be derived from administering serially diluted preparations comprising a composition or medicament of the invention in conjunction with a suitable testing procedure. Additionally or alternatively, a matrix comprising various different dosages and dosage frequency can be designed and applied to one or more groups of experimental subjects to determine optimal dosages.

Generally, an effective dosage is expected to be in the range of about 0.0001 mg to about 1000 mg of active agent per kg body weight per 24 hours; typically, about 0.001 mg to about 750 mg of active agent per kg body weight per 24 hours; about 0.01 mg to about 500 mg of active agent per kg body weight per 24 hours; about 0.1 mg to about 500 mg of active agent per kg body weight per 24 hours; about 0.1 mg to about 250 mg of active agent per kg body weight per 24 hours; or about 1.0 mg to about 250 mg of active agent per kg body weight per 24 hours.

More typically, an effective dose range is expected to be in the range about 1.0 mg to about 200 mg of active agent per kg body weight per 24 hours; about 1.0 mg to about 100 mg of active agent per kg body weight per 24 hours; about 1.0 mg to about 50 mg of active agent per kg body weight per 24 hours; about 1.0 mg to about 25 mg of active agent per kg body weight per 24 hours; about 5.0 mg to about 50 mg of active agent per kg body weight per 24 hours; about 5.0 mg to about 20 mg of active agent per kg body weight per 24 hours; or about 5.0 mg to about 15 mg of active agent per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In many instances, it will be desirable to have several or multiple administrations of a composition or medicament of the present invention. For example, administration may occur 1, 2, 3, 4, 5, 6, 7, 8, 9, 10, or more times. The administrations may be from about one to about twelve week intervals, and in certain embodiments from about one to about four week intervals. Periodic re-administration may be desirable in the case of recurrent exposure to a particular infectious microorganism targeted by a composition or medicament of the present invention.

It will also be apparent to one of ordinary skill in the art that the optimal course of treatment can be ascertained using conventional course of treatment determination tests.

Where two or more therapeutic entities are administered to a subject "in conjunction", they may be administered in a single composition at the same time, or in separate compositions at the same time or in separate compositions separated in time.

The efficacy of methods for preventing or treating diseases referred to herein may be determined using standard techniques.

For therapeutic applications, such a determination will generally rely on establishing whether a given disease is cured or at least partially arrested in the treated subject.

For preventative applications, such a determination will generally rely on establishing whether the subject develops a given disease over a relevant time period following treatment.

These factors may be established by clinical examination of the subject for symptoms and manifestations of the disease in question (e.g. osteoporosis).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting.

Example 1

Characterisation of Gene Profile in Osteogenic Differentiating MSC Induced by IFNγ

Materials and Methods

Human mesenchymal stem cells (MSC) (BioWhittaker, Walkersville, Md., USA) were plated at a density of 5×10$^5$ cells per well in 150 cm$^2$ dishes containing MSC growth medium (GM) (BioWhittaker, Walkersville, Md., USA) with 10% fetal calf serum (FCS) and incubated at 37° C. After the cells reached 60% confluence, media was replaced with either GM or osteoblastogenesis induction media (OIM) (prepared with MSCGM, 10% FCS, 0.2 mM dexamethasone, 10 mmol/L β glycerol phosphate and 50 μg/mL ascorbic acid) for 21 days. Media was changed every three days. Media obtained at the beginning of the 1st, 2nd and 3rd wk of differentiation as well as conditioned media were collected for measurement of IFNγ. Concentrations of IFNγ in the conditioned media were measured from both GM and OM treated cells using Human NT-4 DuoSet ELISA Development Kit (R&D Systems, Minneapolis, Mich., USA). To compare between the osteogenic and the immune effect of IFNγ, Jurkat cells and human T lymphocytes were were plated at a density of 5×10$^5$ cells per well in 150 cm$^2$ dishes containing RPMI media.

Cells were treated with either IFNγ (100 nM) or vehicle for two weeks. At week 2, total RNA was extracted from treated MSC, Jurkat T lymphocytes using an Easy-Kit mini prep (Qiagen, Valencia, Calif., USA). Generation of cDNA, fluorescent labeling, hybridization to the gene chip and data analysis were performed by the Genomics Laboratory at Ramacciotti Institute (Sydney, Australia). 12,000 human genes were examined and expressed sequences tags (ESTs) on the array Human Genome U95A (Affymetrix, Inc. Santa Clara, Calif., USA) and analyzed the results using the MicroDB™ Software (Affymetrix, Inc. Santa Clara, Calif., USA). Expression values of the differentiated and non-differentiated MSC and between MSC vs. Jurkat cells and T lymphocytes were compared using Student's t test. Genes with significant changes were then grouped depending on their known function. The biological function of each gene product was obtained from literature searches in medical databases. This experiment was repeated twice and significant changes in gene expression determined by the method of biological duplicates.

Results and Discussion

A cDNA gene array analysis was performed in MSC induced to differentiate into osteoblasts using osteogenic media for 7 days while being treated with an anabolic dose of IFNγ (100 nM) in vitro. A comparison of was made of cDNA data obtained from differentiating MSC, human primary T-lymphocytes and Jurkat cells either untreated or treated with IFNγ (FIG. 1). The aims of this approach were not only to characterise the osteogenic effect of IFNγ on osteogenic differentiating MSC, but also to compare the osteogenic vs. the immunogenic profile of IFNγ. Interestingly, as shown in FIG. 1, as part of a very specific "osteogenic profile" of IFNγ in osteogenic differentiating MSC, significantly higher levels of IDO-1 gene expression (12 fold) in the IFNγ-treated differentiating MSC were found as compared with both untreated MSC and immune cells. In contrast, treatment of immune cells with IFNγ induced high levels of TPH-1 gene expression without affecting IDO-1 gene expression (FIG. 1).

Taken together, this gene analysis of the osteogenic vs. immune effect of IFNγ identified IDO-1 as an important target of IFNγ, which is exclusive to osteogenic conditions suggesting an important physiological role and a potential therapeutic effect of increasing IDO-1 activity in osteogenic differentiating MSC.

Figure 2:
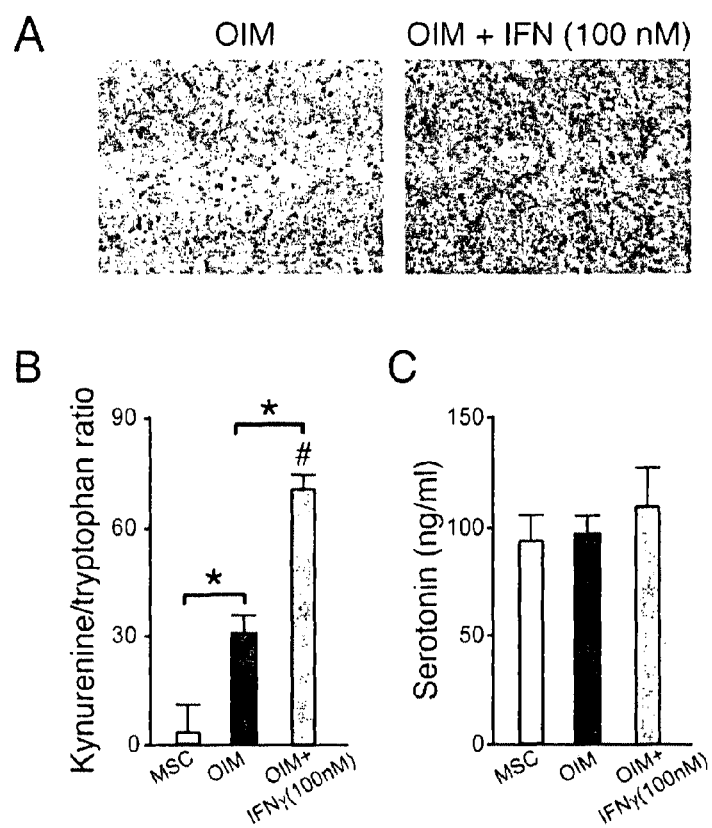
FIG. 2 provides microscopy images (A) and a graph (B) illustrating osteoblastogenesis and activation of the kynurenine pathway of tryptophan degradation. (A) After one week of osteogenic differentiation, MSC treated with IFNγ (100 ng/ml) showed higher levels of mineralization (alizarin red staining) as compared with vehicle-treated cells. (B) This effect corresponds with higher levels of tryptophan degradation in the MSC treated with IFNγ as demonstrated by a higher kynurenine/tryptophan ratio. *$p<0.001$. (C) No changes in serotonin concentrations in the supernatants were found in either treated or untreated cells. Column 1: MSC; Column 2: MSC (OIM); Column 3: MSC (OIM+IFNγ 100 nM). *$p<0.001$, #$p<0.01$ IFNγ treated MSC vs. untreated controls.

It was also determined whether osteoblastogenesis, induced by either treating MSC with osteogenic media or after IFNγ treatment in MSC, was also associated with an increase in the activation of the kynurenine pathway independently of the presence of IFNγ without affecting serotonin secretion into the media. As shown in FIG. 2, the up regulation of IDO-1 in osteogenic differentiating MSC both in IFNγ treated and untreated conditions correlated with higher levels of enzymatic activity of IDO-1 as suggested by high performance liquid chromatography (HPLC) analysis of the kynurenine/tryptophan ratio. In addition, there was no difference in the serotonin concentrations (measured using ELISA) in the supernatants obtained from osteoblastogenesis induction media (OIM)- and IFNγ-treated vs. untreated cells. Taken together, this evidence indicates that activation of tryptophan degradation through IDO-1 is part of the response of MSC to osteogenic conditions. This effect is independent of serotonin concentration in the media.

Figure 3:
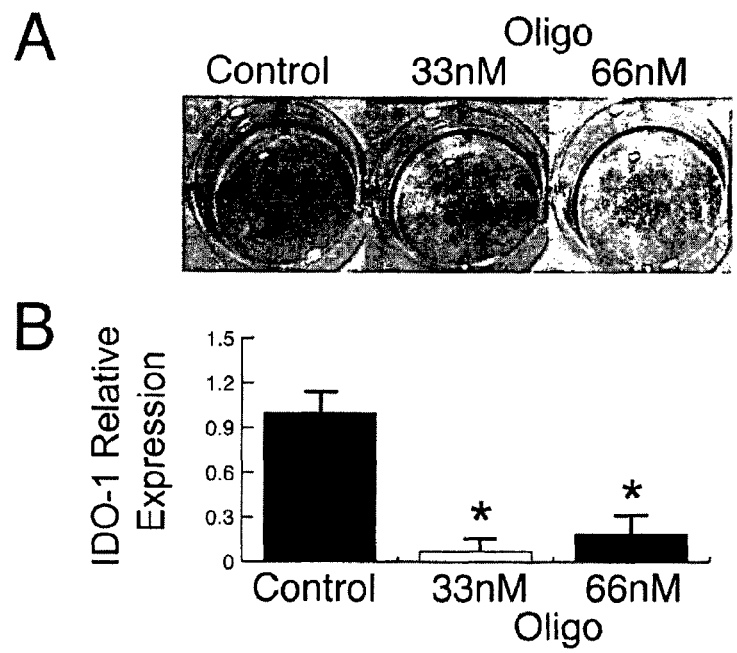
FIG. 3 part (A) shows that IDO-1 siRNA inhibits alkaline phosphatase production and hence osteoblastogenesis indifferentiating MSC. Part B shows IDO-1 gene expression after treating with siRNA with columns 2 (33 nM) and 3 (66 nM) showing more than 70% IDO-1 inhibition when compared to negative control (column 1).
Figure 5:
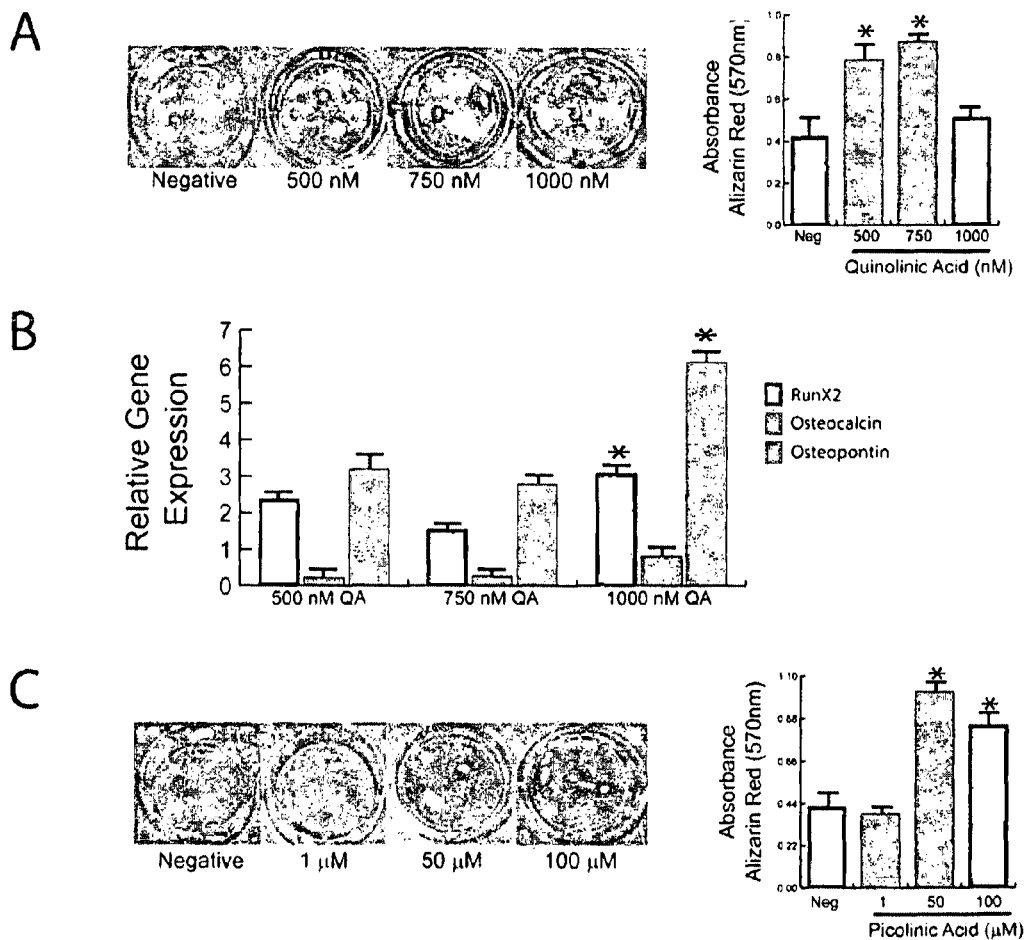
FIG. 5 provides microscopy images indicative of the effect of IFNγ on tryptophan degradation pathway in gut and bone. Eight-month old C57BL/6 mice treated with IFNγ for 6 weeks showed higher levels of IDO-1 in their gut and bone marrow (see top left panel in each of (A) and (B)). In contrast, expression of TPH-1 in gut and bone or of gut derived serotonin were unaffected by treatment with IFNγ.
Figure 5:
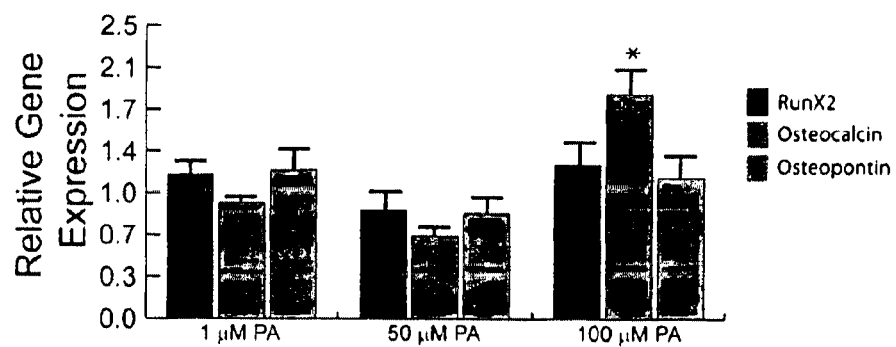
Figure 5:
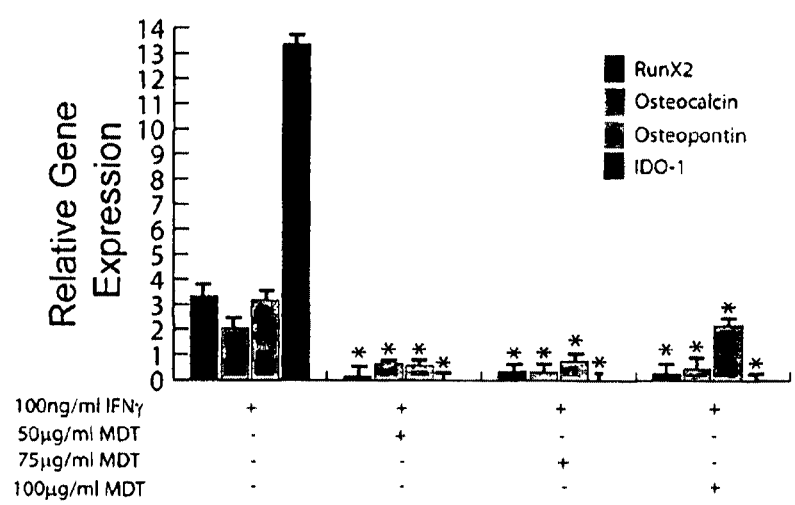

Furthermore, after identification of IDO-1 as one of the the main enzymes activated during osteoblastogenesis in human MSC, assessment of the effect of inhibition of IDO-1 on osteogenic differentiating MSC was conducted using a siRNA model. As shown in FIGS. 3A and 3B, siRNA of the IDO-gene inhibits osteoblastogenesis. Subsequently, differentiating MSC were treated with the end products of the kynurenine pathway, PA and QA, which was performed to assess whether they can facilitate osteogenesis in differentiating MSC in vitro. As shown in FIG. 5, both PA and QA accelerated mineralisation in differentiating MSC. This effect was significantly higher in QA and PA-treated cells.

Taken together the results suggest that regulation of the kynurenine pathway plays an essential role osteoblastogenesis. Either (or both) the direct stimulation of this pathway or treating the cells with the end products of kynurenine activation may have a potent osteogenic effect. In contrast, inhibition of the main enzyme of the kynurenine pathway inhibits osteoblastogenesis Example 2

Effect of IFNγ on Tryptophan Degradation in Bone and Gut of IFNγ-Treated-Mice

To further explore the role of kynurenine pathway in bone formation in vivo, a model of IFNγ-treated OVX mice was used to investigate the effect of IFNγ on tryptophan degradation in bone and gut of IFNγ-treated-mice.

Materials and Methods

Animals were purchased from Jackson Laboratories (Bar Harbor, Me., USA). 8-week-old virgin female C57BL/6 mice (Charles River Laboratories, Quebec, Canada) were used to study the effect of exogenous administration of IFN-γ on bone and gut expression of IDO-1 and TPH-1. Bilateral ovariectomies (OVX) were performed under general anesthesia. Another group of animals was sham-operated (SHAM), in which ovaries were exteriorized but replaced intact. Two weeks after surgery, mice (OVX and SHAM) received intraperitoneal injections of 2000 IU of IFN-γ (R&D Systems, Inc., Minneapolis, Minn., USA) or vehicle (PBS) three times weekly for a total of 6 weeks. Mice were housed in cages in a limited-access room. Animal husbandry adhered to Canadian Council on Animal Care Standards, and all protocols were approved by the McGill University Health Center Animal Care Utilization Committee.

One side femur and proximal gut from each animal in each group was removed at the time of euthanization. Bone was fixed in 70% ethanol, dehydrated, and embedded undecalcified in methyl methacrylate (J-T Baker, Phillipsburg, N.J., USA). At 50-μm intervals, longitudinal sections 5- and 8-μm thick were cut using a Polycut-E microtome (Reichert-Jung Leica, Heerbrugg, Switzerland). Gut was fixed and embedded in paraffin for future analysis. Gut sections were obtained as described above.

For immunohistochemistry, gut and bone sections were incubated overnight at 4° C. with a goat polyclonal antibody IgG against either IDO-1 or TPH-1 (Santacruz Biotechnology Inc. Santa Cruz Calif., USA), Primary antibody was detected by incubation with an anti-goat IgG secondary antibody conjugated with horseradish peroxidase (1:300 in BSA 1%, Sigma-Aldrich, St. Louis, Mo., USA)]. Antibody complexes were visualized with DAB, a 3, 3-diaminobenzine solution containing hydrogen peroxide (Zymed Laboratories Inc., San Francisco, Calif., USA) and then counterstained in 1% hematoxylin. Photographs were taken under an Olympus fluorescence microscope controlled by an IPLab system. Brightness, overlap and contrast adjustments were performed in Photoshop (Adobe).

Results and Discussion

Figure 4:
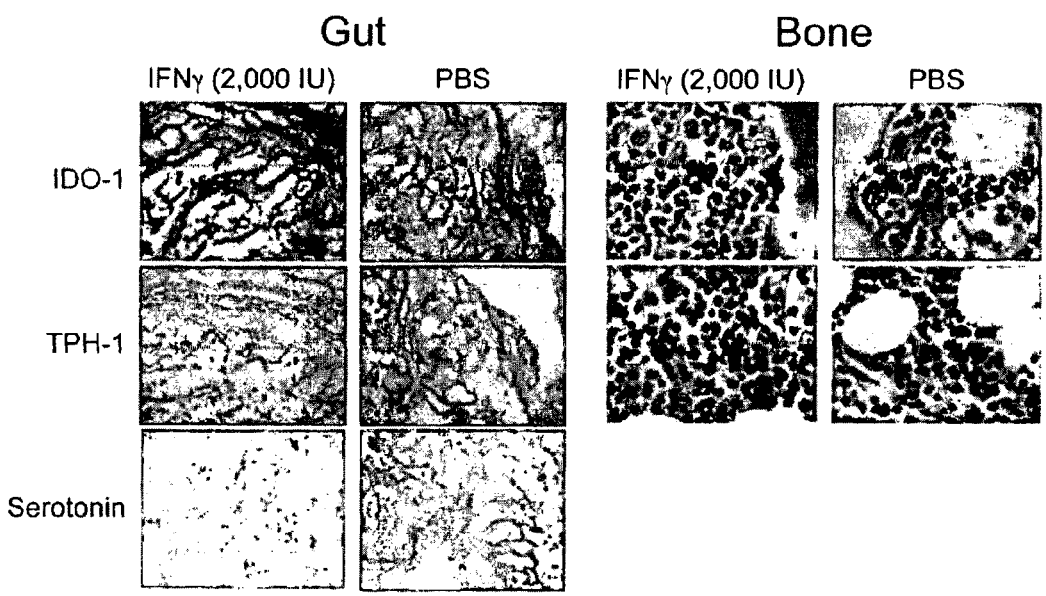
FIG. 4 shows that QA (Parts (A) and (B)) and PA (Parts (C) and (D)) stimulate osteoblastogenesis in MSC induced to differentiate into osteoblasts by treatment with OIM for (2 weeks). Higher levels of alizarin red (AR) (A) and (C) staining indicate higher levels of mineralization. Parts (B) and (D) show the effect of QA and PA, respectively, on osteogenic gene expression. Part (E) shows the effect on osteogenic gene expression when inhibiting IDO-1 with addition of methyl-D-tryptophan *$p<0.001$, treated vs. control.

As shown in FIG. 4, eight-week old C56BL/6 mice treated with IFNγ (2,000 IU/SC/day, 3 times a week for 6 weeks) showed higher levels of IDO-1 in both gut and bone marrow. In contrast, expression of either TPH-1 in gut and bone or GDS in the gut remains unaltered by treatment with IFNγ. Taken together, the in vitro (Example 1 above) and in vivo evidence indicates that: IDO-1 is highly expressed during osteoblastogenesis, and, the kynurenine pathway is activated during osteoblastogenesis both in vitro and in vivo.

In summary, the results provide evidence suggesting that tryptophan degradation plays an important role in bone metabolism. It is intriguing that despite the abundance of evidence on the role of the serotonin pathway in bone formation, there is no prior evidence on the role of the kynurenine pathway in bone metabolism.

Example 3

Identification of the Role of the Elements of the Alternative Pathway of Tryptophan Degradation (Kynurenine Pathway) in Osteoblastogenesis and Bone Formation In Vitro Materials and Methods After identification of the important role of the activation of the kynurenine pathway in osteoblastogenesis both in vitro (Example 1) and in vivo (Example 2) with and without the presence of IFNγ in the media, two approaches were then taken to further assess the role of the elements of the kynurenine pathway in osteoblastogenesis: 1) silencing RNA (siRNA) of the IDO-1 gene in vitro and pharmacological inhibition of IDO-1 activity; and 2) treatment of differentiating MSC with either intermediate or end products of the kynurenine pathway.

For siRNA transfection, MSC were cultured in a 6-well plate at a density of $4 \times 10^3$ cells/well with antibiotic free growth media. After reaching 50-70% of confluence, MSC were induced to differentiate into osteoblasts as previously described. siRNA transfections were started at time 0 of differentiation using the Santa Cruz IDO-1 siRNA kit (sc-35776; Santa Cruz Biotechnology) following siRNA protocols for MSC as previously described (See Akter et al. (2009), "*Effect of lamin A/C knockdown on osteoblast differentiation and function*", J Bone Miner Res. 24(2):283-93). siRNA-untreated cells (plated in either OIM or AIM) and cells treated with control siRNA (sc-37007; Santa Cruz Biotechnology), which contains a scrambled sequence that will not lead to the specific degradation of any known cellular mRNA, were used as controls.

To identify the optimal dose needed for inhibition of IDO-1, different concentrations of oligo were tested. Co-transfection with a fluorescently tagged control siRNA was used to determine the transfection efficiency, and fluorescence microscopy showed a perinuclear localization of the tagged RNA. Texas red-labeled siRNA (siGLO RISCFree siRNA; Dharmacon, Chicago, Ill., USA) was co-transfected with IDO-1 siRNA and visualized using fluorescence microscopy.

At the day of siRNA transfection, siRNA duplex containing solution (solution A) and siRNA transfection reagent (solution B) were prepared according to the manufacturer's protocol. Solutions were mixed and incubated for 45 min at room temperature before use. For each transfection, 0.8 ml siRNA transfection medium was added to each tube containing the solutions mixture. After washing the cells twice with serum and antibiotic free media, 1 ml of siRNA mixtures containing increasing concentrations of oligo (200-800 nM) were added to the cells. After a 5- to 7-h incubation at 37° C. in 5% $CO_2$, 1 ml differentiation media containing 2× serum and antibiotic was added without removing the transfection mixture. Four different conditions were tested: (1) OIM without siRNA; (2) OIM+IDO-1 siRNA (mixture of solution A and solution B); (3) OIM+solution B only; and (4) OIM+control siRNA. Conditions (1), (3), and (4) were used as controls. Finally, after 18-24 h of transfection, media were replaced with OIM with normal concentrations of antibiotic and serum. For osteoblast differentiation of MSC, identification of differentiation was performed with alkaline phosphatase after a total of two consecutive transfections.

Subsequently, the effect of chemical inhibition/stimulation of the intermediate and end products of kynurenine activation on osteogenic differentiating MSC was then characterised. A set of experiments were performed aimed at demonstrating the effect of the different intermediate compounds of the kynurenine pathway after tryptophan degradation by IDO-1 (Table 1).

TABLE 1 compounds to be used for chemical inhibition/stimulation of the kynurenine pathway during osteoblastogenesis

| Pathway (steps) | Compound | Inhibitor | Stimulator | Dosing |
|---|---|---|---|---|
| IDO-1 | INFγ | | X | 100 ng/ml |
| IDO-1 | DI-methyl tryptophan | X | | 50, 75 and 100 µg/ml |
| Kynurenine | L-Kynurenine | | X | 0.25, 0.50 and 0.75 µg/ml |
| Quinolinic acid | Quinolinic acid | | X | 500, 750, 1000 mM |
| Picolinic acid | Picolinic acid | | X | 1, 50, 100 µM |

These compounds were added to the MSC media on day one of differentiation. Cells were treated for six weeks. Media was changed every three days. After three weeks of treatment, osteoblastogenesis and changes in osteogenic genes were quantified as described above.

Results and Discussion

Relative gene expression of RUNX2, OCN and OPN was increased in differentiating MSC treated with either quinolinic or picolinic acid (FIGS. 5 A-D) but not with L-kynurenine (data no shown). After 14 days, relative expression (RE) was 3 and 6 fold higher for RUNX2 and osteopontin in treated cells with 1000 nM quinolinic acid when compared to untreated cells ($p<0.001$). For picolinic acid a significant increase in RE of RUNX2 (1.43) and osteopontin (1.35) and osteocalcin (1.93) was observed 14 days post-induction only when treated with the highest dose (100 µM). The addition of IFNγ to differentiating osteoblasts resulted in a 36 fold increase in IDO-1 expression after 7 days ($p<0.001$) decreasing to 13 fold by the 14th day. At day 14 of differentiation, RE of IDO-1 was decreased to 0.02 when compared to control in the presence of inhibitor (FIG. 5E). All osteogenic genes were concurrently reduced with IDO-1 inhibition ($p<0.001$) Furthermore, inhibition of IDO-1 resulted in a significant decrease in mineralization measured by alizarin red ($p<0.05$).

In summary, the results demonstrate that IDO-1 and the tryptophan degradation pathway play an essential role in osteoblastogenesis and that these compounds are suitable for the development of anabolic therapies for osteoporosis. The osteogenic effect was observed in the presence of the end-products of this pathway (quinolinic and picolinic acid) and not by the intermediate element of the pathway (L-kynurenine) suggesting that the release of these end-products is the pivotal step in osteogenesis after activation of IDO-1.

Example 4

Osteogenic Potential of Bone Marrow Stromal Cells Obtained from IDO-1 KO Mice was Rescued after Treatment with Either Quinolinic or Picolinic Acid Materials and Methods One side tibiae from 9-month-old IDO-1$^{-/-}$ and IDO-1$^{+/+}$ mice (n=6 per group) were flushed using a 21-gauge needle attached to a 10 ml syringe filled with Dulbecco's modified Eagle's medium (DME) (GIBCO BRL, Gaithersburg, Md., USA). The bone marrow cells were filtered through a cell strainer with a 70-micron nylon mesh (BD Bioscience, Bedford, Mass., USA) and plated in 10 cm$^2$ tissue culture dishes. The cells were incubated in growth medium at 37° C. with 5% humidified $CO_2$ and isolated by their adherence to tissue culture plastic. Medium was aspirated and replaced with fresh medium every 2 to 3 days to remove non-adherent cells. The adherent MSC were grown to confluency for about 7 days and defined as MSC at passage 0, harvested with 0.25% trypsin and 1 mM EDTA for 5 min at 37° C., diluted 1:3 in growth medium, plated and grown to confluency for further expansion. After $2^{nd}$ and $3^{rd}$ passages, MSC were used for subsequent experiments.

To induce differentiation, a total of $10^4$ cells were diluted in osteogenic medium and plated in 24 dishes per group in the presence or absence of either quinolinic or picolinic acid. Media was aspirated and replaced with fresh osteogenic medium every 3 days. At 21 days, medium was removed and cultures were fixed in 10% v/v formol/saline solution for 5 min. Cultures were stained with Alizarin Red, which was then extracted and quantified at 570 nm.

Results

Figure 6:
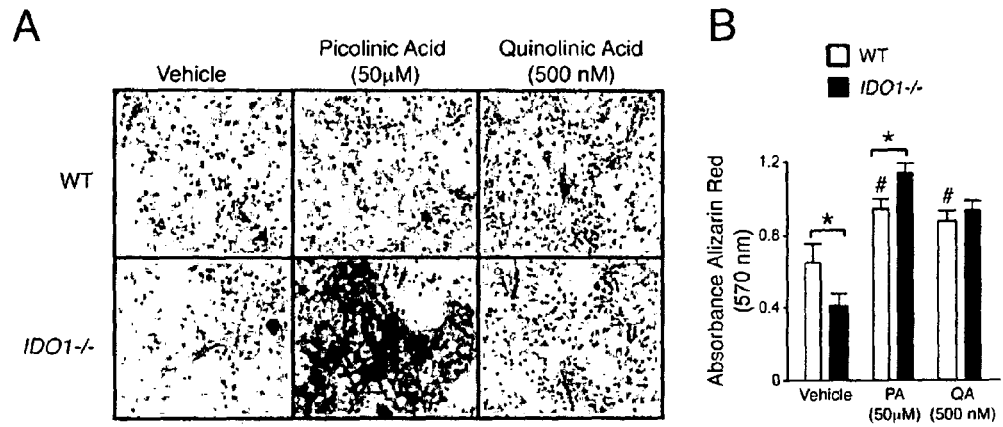
FIG. 6 provides images (A) and a graph (B) indicating that the osteogenic potential of MSC obtained from mice lacking IDO-1 (IDO-1$^{-/-}$) is rescued by exposing bone marrow stromal cells (BMSC) to either picolinic or quinolinic acid. BMSC obtained from IDO-1 KO and WT controls were induced to differentiate into osteoblasts for a week in the presence of PA or QA. Alizarin red staining shows higher levels of mineralisation in the treated conditions as compared with vehicle-treated cells. *$p<0.01$, #$p<0.01$ compared with vehicle-treated WT mice.

FIG. 6 shows compares the osteogenic effect of BMSC under treated vs. untreated conditions. Alizarin red staining shows higher levels of mineralisation in the treated conditions as compared with vehicle-treated cells. *p<0.01, #p<0.01 compared with vehicle-treated WT mice.

Example 6

Bone Phenotype in IDO-1 Knock-Out (KO) Mice

Materials and Methods

Animals—TDO-1 KO mice were developed from a C57BL6/J background and show no phenotypical differences when compared with their wild type (WT) littermates, including same life span.

Quantitative Radiologic Imaging—Micro computed tomography (Micro-CT) was performed in the left femur after removal of soft tissues and overnight fixation in 4% paraformaldehyde. A Skyscan 1172 instrument (Skyscan, Antwerp, Belgium) equipped with a 1.3 Mp camera was used to capture 2D serial cross-sections, which were used to reconstruct 3-dimensional images for the quantification of the volume of bone in the distal metaphysis. Bone microarchitecture measurements were assessed using a set of calibrated phantoms purchased from Skyscan.

Histology and Histomorphometry—For histomorphometric analyses the left femur was fixed overnight in 4% paraformaldehyde, rinsed in 3 changes of PBS and embedded in polymethylmethacrylate (MMA) or a mixture of 50% MMA and 50% glycolmethacrylate (GMA). Serial 4- to 6-µm sections of MMA-embedded tissues were left unstained or stained with von Kossa, while MMA-GMA sections were stained for alkaline phosphatase (ALP) (osteoblasts), toluidine blue (osteocytes), and tartrate resistance acid phosphatase (TRAP) (osteoclasts) activity as described previously. Images were captured using a Leica DMR microscope (Leica Microsystems) equipped with a Retiga 1300 camera (Qimaging, Burnaby, British Columbia, Canada) and the primary histomorphometric data obtained using Bioquant Nova Prime image analysis software (Bioquant Image Analysis Corp, Nashville, Tenn.).

Immunohistochemistry—Gut samples were embedded in low-melting-point paraffin in a Shandon Citadel 2000 automatic tissue processor (Shandon Scientific Limited, Runcorn, UK). Coronary and transverse sections (4µ) were obtained and mounted on silane-coated glass slides (Fischer Scientific, Springfield, N.J., USA) and paraffin was removed with three washes of xylene and rehydrated with ethanol washes (80-50-30%) and PBS. Non-specific binding was blocked by addition of goat serum for 1 hour. Sections were then incubated with mouse monoclonal IgM serotonin antibody (Santa Cruz Biotechnology, Santa Cruz, Calif., USA) for either 4 h at room temperature or 8-24 h at 4° C. After washing with PBS, mouse antibodies to rabbit IgG were added to the sections at room temperature for 30 minutes, followed by a 30 minute incubation with 0.6% hydrogen peroxide+chromogen. Immunohistochemical staining was performed using the human ABC staining system (Santa Cruz Biotechnology, Santa Cruz, Calif., USA).

Results

Figure 7:
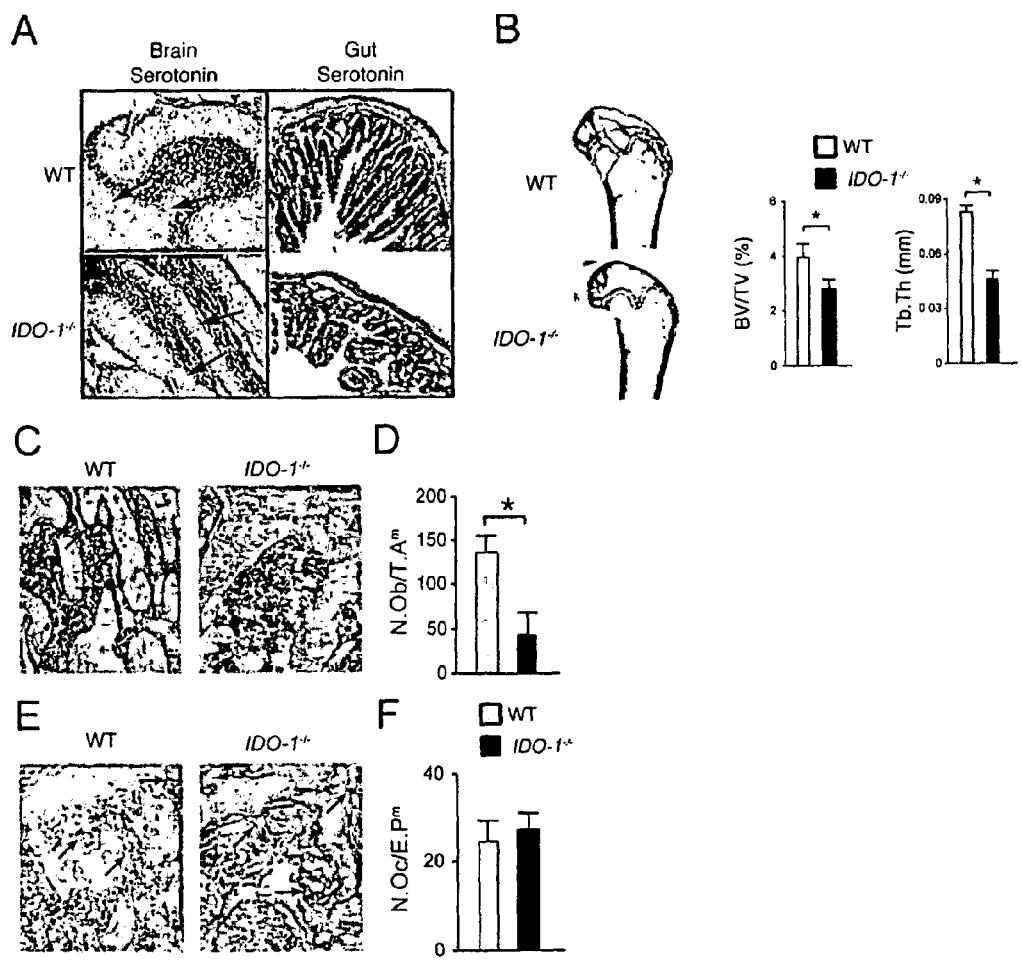
FIG. 7 provides immunohistochemical images and associated graphs demonstrating that IDO-1 KO mice are osteopenic. (A) Immunohistochemistry analysis of serotonin in IDO-1 KO mice compared with WT controls; (B) MicroCT analysis of IDO-1 KO mice compared with WT controls (BV: bone volume; TV: total volume; Tb Th: trabecular thickness; *$p<0.01$); (C-F) Alkaline phosphatase (C) and TRAP (E) staining in IDO-1 KO mice compared with WT controls; (D) osteoblast number in IDO-1 KO mice compared with WT controls; (F) osteoclast number in IDO-1 KO mice compared with WT controls. (*$p<0.01$).

Analysis of the bone phenotype in IDO-1 KO mice showed osteopenia associated with low levels of bone formation (FIG. 7), which were found to be independent of levels of serotonin expression in brain and gut. Immunohistochemistry analysis of serotonin showed no differences in expression in IDO-1 compared with WT controls (FIG. 7A). MicroCT analysis showed that IDO-1 mice are osteopenic as suggested by lower bone volume/total volume (BV/TV) and trabecular thickness (Tb.Th) in the mutant mice (FIG. 7B). Alkaline phosphatase (FIG. 7C) and TRAP (FIG. 7E) staining showed that mutant mice have low osteoblast number (FIG. 7D) with no changes in osteoclast number (FIG. 7F).

Example 7

Therapeutic Uses of Elements of the Kynurenine Pathway in Osteoporosis

Materials and Methods

Figure 8:
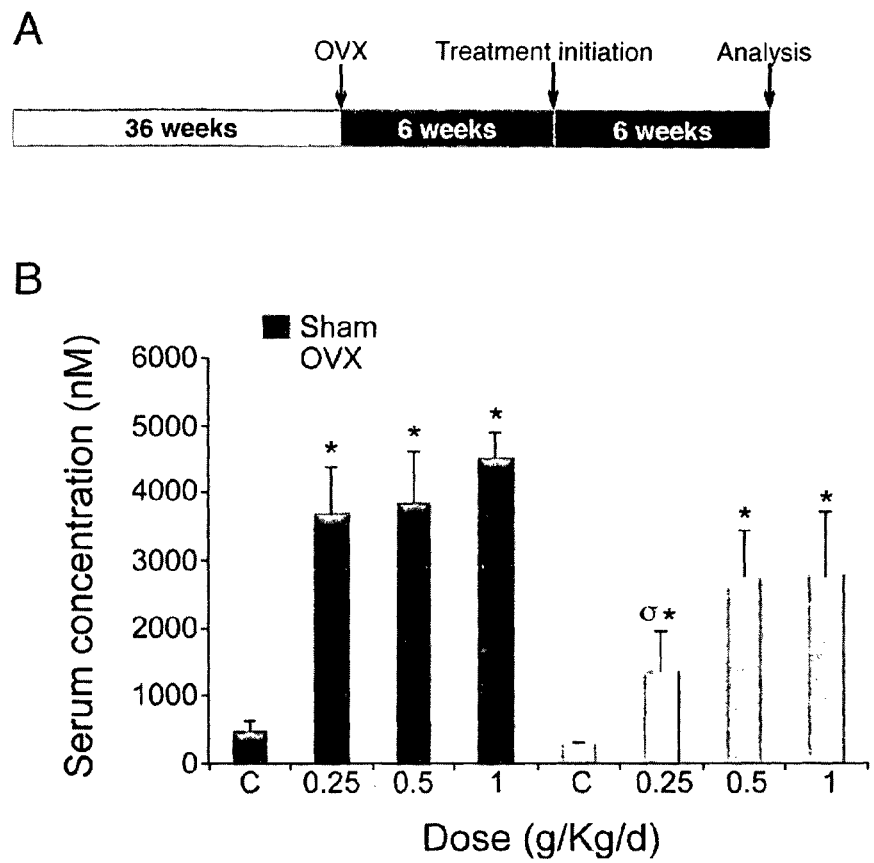
FIG. 8 shows pharmacokinetics of oral PA in OVX mice. (A) Study design (B) Serum concentrations (nM) of PA in mice treated with oral PA. Columns 1-4 (Sham); columns 5-8 (OVX); *$p<0.001$ treated vs. control mice within their corresponding group; σ $p<0.05$ low dose PA in OVX vs. Sham operated mice.

In view of the results provided in the Examples above, a mouse model of OVX C57BL/6 mice was used to investigate the effects of treatment with PA for 6 weeks (FIG. 8A). In comparison to the LP533401, which inhibits an enzyme that is required in several biological functions including gut motility, the present approach was postulated to be significantly safer with a higher translational potential into human studies. The rationale for this was: 1) Instead of inhibiting a biologically required enzyme, the present approach uses the enzymatic end products without affecting the enzyme, which is required for other physiological processes; 2) PA is safe when used in animal models; and, 3) tolerability will be excellent since PA is a vitamin-like and water soluble compound, which facilitates its pharmacokinetics and pharmacodynamics.

(i) Animals

Nine-month-old oophorectomised (OVX) and SHAM-operated C57BL/6 mice (n=24 per group) were obtained from the Animal Resources Centre (Perth, Wash.). After 2 weeks of acclimation, mice were divided into four groups (Table 2) and received treatment in their drinking water for a total of 6 weeks. Mice treated with plain water were used as controls. Mice were housed in cages in a limited access room.

TABLE 2

Experimental Mice Groups

A-SHAM operated

Vehicle-treated SHAM controls (n = 6)
SHAM PA low dose (250 mg/kg/d) (n = 6)
SHAM PA mid dose (500 mg/kg/d) (n = 6)
SHAM PA high dose (1 gm/kg/d) (n = 6)

B-OVX mice

Vehicle-treated OVX controls (n = 6)
OVX PA low dose (250 mg/kg/d) (n = 6)
OVX PA mid dose (500 mg/kg/d) (n = 6)
OVX PA high dose (1 gm/kg/d) (n = 6)

(ii) Reagents, Antibodies, and Media.

PA was purchased from Sigma (Sigma-Aldrich, Sydney, NSW, Australia). Cell culture reagents were purchased from Sigma (Sigma-Aldrich, Sydney, NSW, Australia) unless otherwise specified. Antibodies for western blotting were obtained from Santa Cruz Biotechnology (Santa Cruz, Calif.).

(iii) Radiography and µ-CT Analysis

Mice were administered a lethal dose of anaesthetic at the indicated times, exsanguinated, and imaged using a Faxitron MX20 equipped with an FPX-2 Imaging system (Dalsa Medoptics, Waterloo, Ontario, Canada). µ-CT was performed on the left femur and lumbar vertebrae after removal of soft tissues and overnight fixation in 4% paraformaldehyde. The distal metaphysis of the femur and the body of the vertebrae were scanned with a Skyscan 1072 micro-CT instrument (Skyscan, Antwerp, Belgium). Image acquisition was performed at 100 kV and 98 µA, with a 0.9° rotation between frames. The two-dimensional images were used to generate three-dimensional reconstructions to obtain quantitative data with the 3D Creator software supplied with the instrument. Nomenclature and abbreviations of 3D-µCT parameters follow the recommendations of the American Society of Bone and Mineral Research (see Bouxsein et al. (2010), "*Guidelines for assessment of bone microstructure in rodents using micro-computed tomography*", J Bone Miner Res., 25: 1468-1486).

(iv) Histological and Histomorphometrical Analysis of Bone

For dynamic histomorphometry, tetracycline labelling was achieved through the intraperitoneal injection of demeclocycline (20 mg/kg) (Sigma Chemicals, St. Louis, Mo., USA) to the three treated groups at 5 and 2 days before sacrifice. One side femur from each animal in each group was removed at the time of killing, fixed in 70% ethanol, dehydrated, and embedded undecalcified in methylmethacrylate (J-T Baker, Phillipsburg, N.J., USA). At 50 µm intervals, longitudinal sections of 5 and 8 µm thick were cut using a polycut-E microtome (Reichert-Jung Leica, Heerbrugg, Switzerland), placed on gelatine-coated glass slides, deplastified and stained with Goldner's trichrome. Histomorphometry was done with a semi-automatic image analysing system combining a microscope equipped with a camera lucida and digitizing tablet linked to a computer using the OsteoMeasure Software (Osteometrics Inc., Decatur, Ga., USA). Nomenclature and abbreviations of histomorphometric parameters follow the recommendations of the American Society of Bone and Mineral Research (see Parfitt et al. (1987), "*Bone histomorphometry: Standardization of nomenclature, symbols and units*", J Bone Miner Res., 2: 595-610.)

(v) Gas Chromatography-Mass Spectrometry (GC-MS)

For absorption analysis of minerals in the duodenum, tissue was dissected and left to dry up in room temperature. 100 mg of tissue were dissolved in nitric acid and concentrations of nine minerals was quantified in the tissue homogenates using an Agilent 5973 mass selective detector via an auto-sampler Agilent Technologies 7683, and controlled using Agilent ChemStation software (Agilent, Santa Clara, Calif., USA). For pharmacokinetic analysis of PA, serum of Pa- and vehicle-treated animals was obtained by centrifugation. 1 µl of serum was injected into an Agilent 6890 gas chromato-graph, interfaced to an Agilent 5973 mass selective detector via an auto-sampler Agilent Technologies 7683, and controlled using Agilent ChemStation software (Agilent, Santa Clara, Calif., USA).

(vi) Biochemical Analysis

Mice were euthanized at week 6 of treatment, and blood was removed by cardiac puncture. Calciotropic hormones were measured using specific kits for PTH (Immunotopics Inc San Clemente, Calif., USA) and 25(OH)D (ImmunoDiagnostic Systems Ltd, UK). Osteocalcin (OCN) was measured in 20 µl of serum using the mouse OCN immunoradiometric assay kit (Immutopics, San Clemente, Calif., USA). TRAP was measured in 20 µl of serum to assess osteoclastic activity using the Mouse TRAP Assay kit (Immunodiagnostic Systems Ltd., Scottsdale, Ariz.).

(vii) Western Blot Analysis

Marrow cells were obtained from the left femur of PA- and vehicle-treated animals (n=6 per group) by flushing with Dulbecco's alpha modified medium (DMEM). Red blood cells in marrow cells were hemolyzed in 0.017 M tris-HCl, pH 7.5, buffer containing 0.8% ammonium chloride. Hemolyzed bone marrow suspensions were rinsed twice with phosphate buffered saline (PBS). Protein extracts were obtained after suspending the cells in 2 volumes of buffer containing 10 mM EDTA, 0.5 mM phenylmethylsulfonyl fluoride, and one Complete™ protease inhibitor mixture tablet (Boehringer Mannheim, Laval, Quebec, Canada). Solutions were then centrifuged at 25,000×g for 20 min at 4° C.: resuspended in 20 mM HEPES, pH 7.9, 25% glycerol, 0.42 M NaCl, 1.5 mM $MgCl_2$, 0.2 mM EDTA, 0.5 mM phenylmethylsulfonyl fluoride, and 0.5 mM dithiothreitol. Protein content was determined with a protein assay kit (Bio-Rad. Mississauga, Ontario), and samples were then aliquoted and stored at −80° C. For western blot analysis, lysates were dissolved in SDS electrophoresis buffer (Bio-Rad, Hercules, Calif., USA) and proteins separated on SDS-polyacrylamide gels and subsequently electrotransfered to polyvinylidene difluoride membranes. After blocking with PBS containing 0.1% Tween 20 and 10% non-fat dry milk, membranes were incubated overnight at 4° C. using mouse monoclonal antibodies directed against Runx2, and osteocalcin (OCN) (1:1000, Santa Cruz Biotechnology, Santacruz, Calif., USA). Secondary antibodies conjugated to horseradish peroxidase were from Sigma (1:5000). Antigen-antibody complexes were detected by chemiluminescence using a kit of reagents from ECL (Amersham, UK) and blots were exposed to high-performance chemiluminescence film (Amersham, UK). Films were scanned and the optical density of each specific band analysed using the ImageMaster program and expressed as OD/mm2/100 µg of total protein. Relative intensity of the samples was determined comparing the protein of interest in the treated mice using the values of vehicle-treated mice as controls (100%). Values are reported as the average of samples obtained from six mice.

(viii) Ex-Vivo Cultures of Bone Marrow Cells

To establish adherent bone marrow cultures, both tibiae from PA- and vehicle-treated animals (n=6 per group) were flushed using a 21-gauge needle attached to a 10 ml syringe filled with Dulbecco's modified Eagle's Medium (DMEM) (GIBCO BRL, Gaithersburg, Md., USA). Cells from both tibiae were filtered through a cell strainer with 70-micron nylon mesh (BD Bioscience, Bedford, Mass., USA) and then combined to produce a volume of 2 ml containing ~$10^7$ cells/ml. Six-well plate cultures were then established in triplicate, with each well containing a 100-µl aliquot of cell suspension combined with 4 ml of fresh -MEM medium. The cells were incubated in MSC growth media at 37° C. with 5% humidified $CO_2$ and isolated by their adherence to tissue culture plastic. Medium was aspirated and replaced with fresh medium to remove non-adherent cells every 2 to 3 days. The adherent MSC were grown to ~80% confluence for about 7 days defined as MSC at passage 0, harvested with 0.25% trypsin and 1 mM EDTA for 5 min at 37° C., diluted 1:3 in MSC growth media, plated and grown to confluence for further expansion. After $2^{nd}$ and $3^{rd}$ passages, MSC were used for subsequent experiments.

To induce differentiation, a total of $10^4$ cells were diluted in osteogenic medium (prepared with DMEM, 10% FCS, 0.2 mM dexamethasone, 10 mmol/L β glycerol phosphate and 50 µg/mL ascorbic acid) and plated in six well plates. Media was aspirated and replaced with fresh osteogenic medium every 3 days. After 14 days in culture, cells were washed with PBS, ethanol fixed, stained for either alkaline phosphatase (osteoblast differentiation), in which case the cells were counterstained with haematoxylin (Sigma), or alizarin red (mineralisation). For alkaline phosphatase quantification, the colonies with more than 10% of cells staining positive for ALP were considered as colony forming units-osteoblasts (CFU-OB). For alizarin red quantification, matrix mineralization was quantified by extracting the Alizarin red staining with 100 mM cetypyridinium chloride (Sigma, St. Louis, Mo., USA) at room temperature for 3 h. The absorbance of the extracted Alizarin red S staining was measured at 570 nm.

(ix) Semi-Quantitative Real Time Polymerase Chain Reaction (RT-PCR)

Bone marrow cells were flushed and isolated as previously described. Total RNA was extracted from marrow cells using a QIAGEN RNeasy Mini extraction kit following manufacturer's instructions (QIAGEN Pty, Doncaster, VIC, Australia; cat#74104). First strand complementary DNA (cDNA) synthesis was performed using 200 ng of total RNA, 50 ng random hexamers and 50 units reverse transcriptase at 42° C. for 1 hour, as described by manufacturer (Bioline Australia Pty, Alexandria, NSW, Australia; cat# BIO-65025). Real-time PCR for expressed genes as markers for osteogenesis was performed in duplicate in a total reaction volume of 25 µl, 10% of which was cDNA (or water for non-template control), 3 mM $MgCl_2$ and 250 nM of each forward and reverse specific primer for target genes and normalizer. Primers for specific detection of mRNA expression included:

runt-related transcriptional factor 2 (RUNX2)

```
                                        (SEQ ID NO: 1)
F: 5'-GCCGGGAATGATGAGAACTA-3', (SEQ ID NO: 2)
R: 5'-GGACCGTCCACTGTCACTTT-3';
```

OCN

```
                                        (SEQ ID NO: 3)
F: 5'-CTTGGTGCACACCTAGCAGA-3';

(SEQ ID NO: 4)
R: 5'-ACCTTATTGCCCTCCTGCTT-3'.
```

All PCRs were performed in a Corbett Rotor-Gene™ 3000 (QIAGEN Pty) using SYBR green with no-ROX reaction mix and a standard thermal profile as described by supplier (Bioline Australia Pty, Alexandria, NSW, Australia; cat# QT6750-02). Quantitative RT-PCR data was defined by threshold cycle (Ct) normalized for the housekeeping gene glyceraldehyde-3-phosphate dehydrogenase (GAPDH):

```
                                        (SEQ ID NO: 5)
F: 5'-GAAATCCCATCACCATCTTCC-3'

(SEQ ID NO: 6)
R: 5'-AAATGAGCCCCAGCCTTCTC-3'.
```

(x) Statistical Methods

The mice sample size for each experiment, was calculated based on a β error of 0.2 and an α error of 0.05 with a significant power >90% to detect a 10% absolute difference in the parameters of bone formation (BMD, osteoblast numbers, serum levels of bone biomarkers and dynamic histomorphometry). Results of the cell culture experiments were expressed as the standard error of the mean (±SEM). Cell culture experiments will be performed in triplicate and repeated three times. Differences between groups were determined using Levene's test for homogeneity of variances and unpaired t-test for equality of means for histomorphometry measurements, all other variables were compared using one-way analysis of variance (ANOVA). A value of $p<0.05$ was considered significant.

Results (i) Pharmacokinetics of Oral PA in OVX Mice

Serum concentrations of PA were measured using GC-MS as previously described. As shown in FIG. 8B, serum concentrations of PA were increased in the treated groups in a dose-dependent manner. Mice treated with oral PA showed significantly higher serum concentrations of PA as compared with vehicle-treated animals. OVX mice treated with low dose of PA showed lower serum concentrations as compared with their SHAM counterpart. Higher dose of PA was not followed by higher serum concentrations suggesting that a dose of 0.5 gm/Kg/d is sufficient to obtain appropriate and steady serum concentrations (FIG. 8B).

(ii) Therapeutic Safety of Oral PA in OVX Mice

Table 3 shows the comparison in weight and water consumption between PA- and vehicle-treated mice. PA-treated mice showed no difference as compared with their vehicle-treated controls. In addition, the mice survival rate was 100% with no evidence of side effects in the treated groups. Taken together, this evidence suggests that PA is a safe and well-tolerated treatment.

TABLE 3

Weight comparison between groups after 6 weeks of treatment.

| Group (treatment-dose) | Weight (gm) | Water left (ml/week) | p |
|---|---|---|---|
| Sham control | 26 ± 1.3 | 175 ± 25 | NS |
| Sham (PA250) | 27 ± 2.0 | 200 ± 32 | NS |
| Sham (PA500) | 26 ± 2.4 | 155 ± 35 | NS |

TABLE 3-continued

Weight comparison between groups after 6 weeks of treatment.

| Group (treatment-dose) | Weight (gm) | Water left (ml/week) | p |
|---|---|---|---|
| Sham (PA1000) | 26 ± 1.3 | 260 ± 45 | NS |
| OVX Control | 28 ± 1.9 | 175 ± 32 | NS |
| OVX (PA250) | 26 ± 1.6 | 195 ± 28 | NS |
| OVX (PA500) | 28 ± 0.4 | 195 ± 35 | NS |
| OVX (PA1000) | 26 ± 1.3 | 250 ± 38 | NS |

Water left in the bottle (initial volume of 500 mL) was also quantified every week. The table shows the average of water volumes left over every week for the whole duration of the treatment. These volumes correspond with the drinking pattern previously reported in this mouse model.

(iii) Effect of Oral PA on Mineral Absorption in OVX Mice

Figure 9:
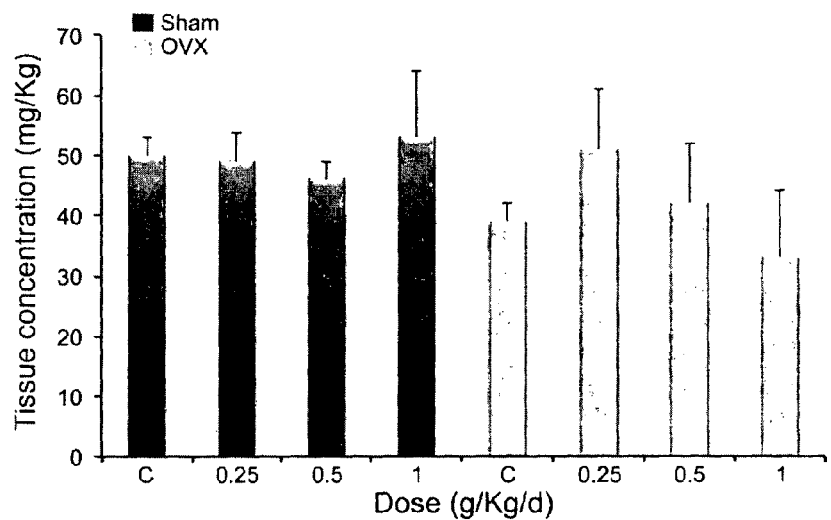
FIG. 9 is a graph showing tissue concentrations of Zn in the duodenum of Sham and OVX mice treated with either PA or vehicle. No difference was found between the eight groups indicating that the therapeutic effect of PA on bone is independent of Zn absorption in the gut. Columns 1-4 (Sham); columns 5-8 (OVX).

A comprehensive quantification of serum concentrations of nine minerals and duodenal concentrations of Zn in the gut was performed as measured by GC-MS. Table 4 and FIG. 9 show no difference in either serum or gut in PA-treated mice as compared with vehicle-treated controls. The observation that no difference was found between the eight groups indicates that the therapeutic effect of PA on bone is independent of Zn absorption in the gut.

TABLE 4

Serum concentration of nine essential minerals in PA- vs. vehicle-treated mice.

| Mineral | Sham control | Sham (PA250) | Sham (PA500) | SHAM (PA1000) | OVX control | OVX (PA250) | OVX (PA500) | OVX (PA1000) |
|---|---|---|---|---|---|---|---|---|
| Carbon (mEq/L) | 30 ± 0.2 | 29 ± 0.9 | 28 ± 0.2 | 31 ± 1.2 | 30 ± 0.8 | 30 ± 0.5 | 29 ± 1.2 | 28 ± 1 |
| Magnesium (mg/dL) | 3 ± 0.3 | 2.8 ± 0.4 | 2.8 ± 0.25 | 2.8 ± 0.22 | 2.9 ± 0.5 | 2.6 ± 0.35 | 2.4 ± 0.17 | 2.6 ± 0.2 |
| Aluminium (µmol/L) | 4 ± 2 | 7 ± 3 | 4 ± 1 | 5 ± 2 | 4 ± 2 | 2 ± 1.4 | 2.5 ± 0.2 | 4.5 ± 3 |
| Calcium (mg/dl) | 9.2 ± 0.4 | 9.1 ± 0.05 | 8.9 ± 0.28 | 9.1 ± 0.24 | 9.4 ± 0.42 | 9 ± 0.25 | 8.9 ± 0.27 | 8.7 ± 0.07 |
| Manganese (µg/L) | 4 ± 2 | 4 ± 1.6 | 3 ± 0.5 | 4 ± 0.9 | 3.6 ± 1 | 3 ± 0.4 | 5 ± 2.5 | 3 ± 0.6 |
| Iron (µg/dL) | 200 ± 20 | 240 ± 70 | 200 ± 80 | 200 ± 40 | 180 ± 50 | 170 ± 30 | 200 ± 70 | 180 ± 20 |
| Cobalt (µg/L) | 2.3 ± 0.3 | 2.4 ± 6.4 | 2.1 ± 0.2 | 2.2 ± 0.1 | 2.2 ± 0.4 | 2 ± 0.1 | 2 ± 0.2 | 1.9 ± 0.1 |
| Copper (µg/L) | 619 ± 19 | 643 ± 52 | 576 ± 69 | 703 ± 56 | 622 ± 7 | 647 ± 36 | 631 ± 10 | 614 ± 31 |
| Zinc (µg/dL) | 73 ± 2.1 | 63 ± 5.2 | 62 ± 7.4 | 69 ± 9.3 | 67 ± 1.6 | 72 ± 6 | 69 ± 7.7 | 73 ± 2.4 |

(iii) Effect of Oral PA on Calciotropic Hormones.

To determine whether the effect of PA on bone was not associated with changes in calciotropic hormones, serum concentrations of vitamin D and PTH were quantified in both PA- and vehicle-treated animals. As shown in Table 5, mice treated with oral PA showed no difference in serum concentrations of calciotropic hormones as compared with their vehicle-treated controls.

TABLE 5

Serum concentrations of calciotropic hormones (vitamin D and PTH) in PA- vs. vehicle-treated mice.

| Group (treatment-dose) | Vitamin D (nmol/L) | PTH (pg/ml) | p |
|---|---|---|---|
| Sham control | 52 ± 13 | 36 ± 6 | NS |
| Sham (PA250) | 54 ± 12 | 40 ± 3 | NS |
| Sham (PA500) | 52 ± 14 | 35 ± 5 | NS |
| Sham (PA1000) | 53 ± 13 | 36 ± 5 | NS |
| OVX Control | 56 ± 19 | 34 ± 6 | NS |
| OVX (PA250) | 52 ± 16 | 35 ± 8 | NS |
| OVX (PA500) | 56 ± 4 | 35 ± 6 | NS |
| OVX (PA1000) | 52 ± 13 | 40 ± 2 | NS |

(iv) Treatment of OVX C57Bl6 Mice with PA Increases Bone Mass and Stimulates Bone Formation.

Figure 10:
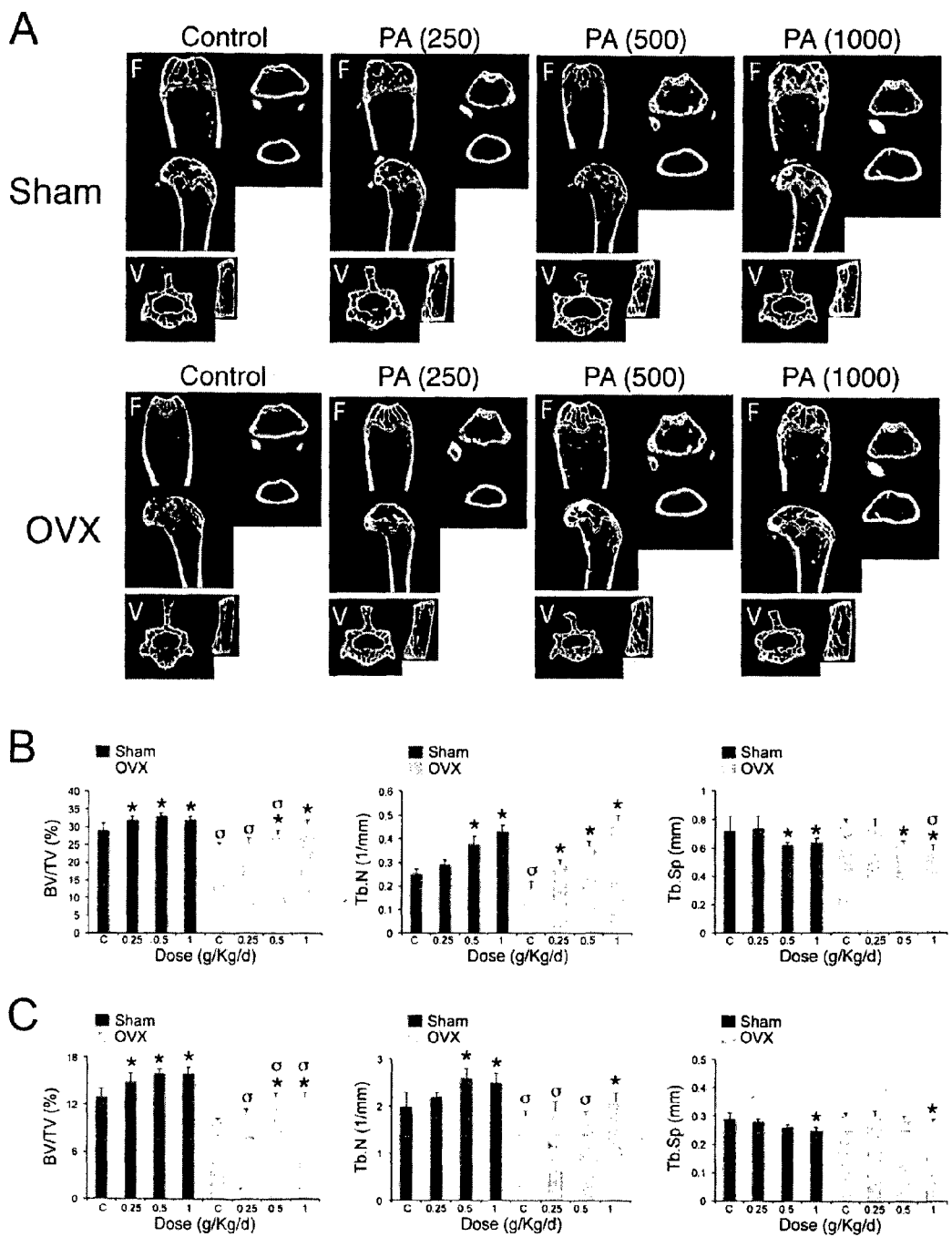
FIG. 10 shows quantitative μCT data indicating that a significant and dose-dependent increase in bone relative to tissue volume (BV/TV) in the region of interest, which was reflected in both increased numbers (Tb.N) and separation (Tb.Sp) of trabeculae in both Sham and OVX mice treated with PA. This effect was observed in both femur (F) and vertebrae (V) of mice treated with the two higher doses of PA. *$p<0.01$ treated vs. control mice within their corresponding group; a $p<0.01$ OVX vs. their corresponding dose group of Sham operated mice.
Figure 11:
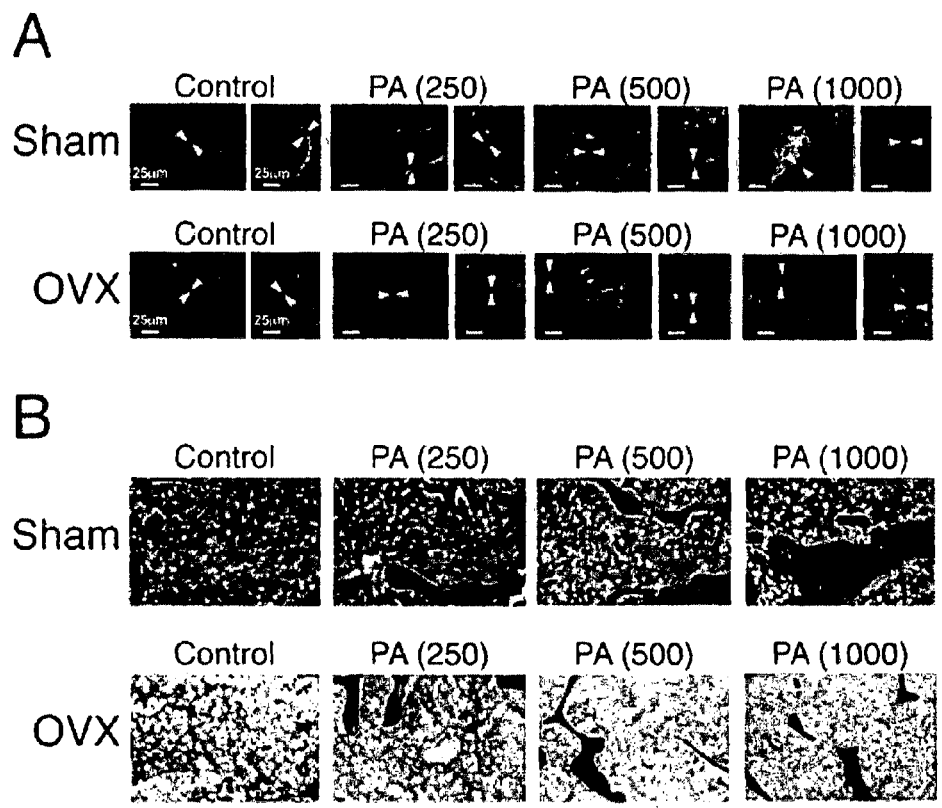
FIG. 11 part (A) Fluorochrome labelling of bone turnover indicated a significant and dose-dependent increase in bone turnover (double labelling, arrows) in both Sham and OVX mice treated with PA. (B) Von Kossa labelling for bone histomorphometry indicating levels of mineralized bone in PA-treated animals compared to untreated controls.

Quantitative µCT data (FIG. 10) indicated a significant and dose-dependent increase in bone relative to tissue volume (BV/TV) in the region of interest, which was reflected in both increased numbers (Tb.N) and thickness (Tb.Th) of trabeculae in both Sham and OVX mice treated with PA. Von Kossa staining of undecalcified bone confirmed these results (FIG. 11). As shown in FIG. 11A, fluorochrome labelling of bone turnover indicated a significant and dose-dependent increase in bone turnover (double labelling, arrows) in both Sham and OVX mice treated with PA. Furthermore, dynamic histomorphometry performed on tetracycline labelled sections (FIG. 11) revealed increased mineral apposition rates (MAR) in both trabecular and cortical bone in the mice receiving PA compared with vehicle treated control. As shown in FIG. 11B, Von Kossa labelling for bone histomorphometry showed higher levels of mineralized bone in the PA-treated animals as compared with their untreated controls.

(v) Treatment with PPARγ Inhibitors In Vivo Results in Increased Osteoblastogenesis in Bone Marrow Stromal Cells (BMSC) Cultured Ex Vivo.

Figure 12:
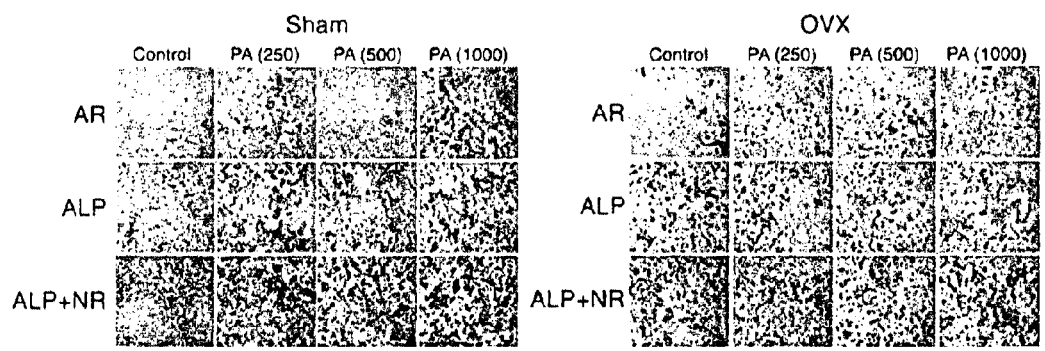
FIG. 12 provides images of ex vivo cultures of BMSC obtained from SHAM and OVX C57BL6 mice mice tibiae after 2 weeks of culture in osteogenic media and treated with PA, as compared to the untreated controls (AR: Alizarin red; ALP: Alkaline Phosphatase, NR: Neutral red).

To determine if the increased number of osteoblasts was related to differentiation of BMSC down the osteoblast lineage, stromal cells were isolated from bone marrow of mice treated for 6 weeks with either vehicle or increasing doses of PA. BMSC were maintained for two weeks in osteogenic medium before quantifying the number of alkaline phosphatase (ALP) positive colonies (FIG. 12). After 2 weeks of culture in osteogenic media, ex vivo cultures of BMSC obtained from mice tibiae showed that both SHAM and OVX C57BL6 mice treated with PA have a significantly capacity to mineralise (AR: Alizarin red) and showed higher number of bone forming units (ALP: Alkaline Phosphatase, NR: Neutral red) as compared to the untreated controls (results from 6 mice per group) (FIG. 12). The number of colony forming units-osteoblasts (CFU-OB), an indicator of the capacity of BMSC to differentiate into osteoblasts, was thus significantly higher in cultures harvested from PA—treated mice compared with those from vehicle treated mice (FIG. 12).

Figure 13:
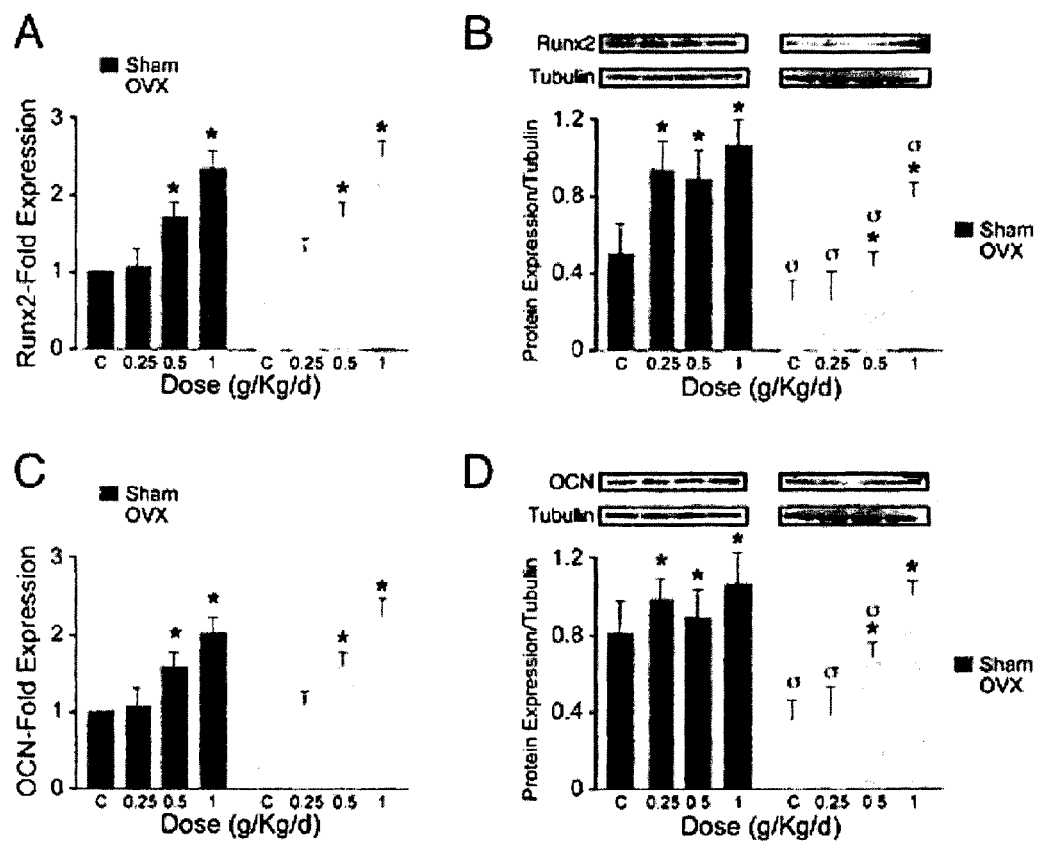
FIG. 13 provides a series of graphs summarising the effects of PA treatment on osteogenic genes. (A) and (C): effect of PA on Runx2 (A) and osteocalcin (OCN) (C)

FIG. 13 shows the effects of PA treatment on osteogenic genes. mRNA and total protein were obtained from bone marrow flushed from tibiae of PA- and vehicle-treated animals. RT-PCR analysis of messenger RNA extracted from bone marrow cells showed higher levels of the osteogenic genes Runx2 and OCN in all the PA-treated groups as compared with their vehicle-treated controls (FIGS. 13A and 13C). Hence, treatment with PA affects transcription of both Runx2 and osteocalcin (OCN) as suggested by lower levels of gene expression after correction with housekeeping gene (GAPDH). Immunoblot analysis (FIGS. 13B and 13D) of protein extracted from bone marrow cells revealed a significant increase in expression of OCN and the osteoblast transcription factor Runx2.

DISCUSSION (i) Summary and Interpretation of the Results

Biosafety: excellent tolerability and absorption with no evidence of side effects;

Therapeutic class effect: the effect of PA seems to be specific for this compound as suggested by no cross-related effect on mineral absorption or serum levels of calciotropic hormones;

Targeted cell specific response: the ex vivo and histology experiments allow the conclusion that PA has a strong effect on bone turnover facilitating mineral apposition at both cortical and trabecular bone;

Effect on both aged and OVX animals: this is a very important effect since PA was not only able to rescue OVX mice from osteoporosis but also induced bone formation in normally aged animals. This effect was also more evident on femur than vertebrae suggesting that PA could become an effective treatment to prevent hip fractures due to its strong positive effect on bone formation;

Mechanism of action: in agreement with the in vitro data, in vivo experiments confirmed that treatment with PA induces high expression of osteogenic genes, in this case OCN and Runx2.

Taken together, this evidence clearly indicates that PA has a strong anabolic effect on bone in both aged and OVX mice offering a new therapeutic approach to osteoporosis in the future.

(ii) Significance

Ageing well and healthy is one of the national research priorities in Australia. Unfortunately, osteoporosis is affecting the quality of life of our older persons; therefore the development of new treatments targeted on this population should become a research priority. Treatments for osteoporosis have mostly targeted the inhibition of bone resorption with significant achievement in preventing bone loss. However, due to the particular characteristics of osteoporosis in the elderly, finding anabolic factors for the treatment of osteoporosis has been challenging. In this project, new knowledge was generated on the understanding of a regulatory pathway of bone metabolism that was not been tested in the past. A significant amount of new data on the role of the kynurenine pathway in bone was obtained facilitating the development of new treatments for osteoporosis using a new anabolic mediator of bone formation.

Prophetic Example 8

Further Characterization of the Molecular Mechanisms of Osteoblastogenesis Activated by the Elements of the Alternative Pathway of Tryptophan Degradation (Kynurenine Pathway) During Osteoblastogenesis and Bone Formation In Vitro The experiments described in Example 8 are intended to be performed in the future for the purpose of further confirming the role of the kynurenine pathway in osteoblastogenesis and exemplify the use of kynurenine activation in the anabolic treatment of osteoporosis.

The same model of human MSC (Lonza Biosciences, Mt. Waverley, VIC, Australia) differentiation into osteoblasts will be used. This commercially available model is a well-established model of MSC differentiation. The cells will be obtained from young male volunteers (25-28 year-old). MSC from young human subjects are preferred in order to profit from their higher differentiation potential and to facilitate their response to siRNA transfection. For osteoblastogenesis, after 60% confluence, media will be replaced with either MSC growth media (MSCGM) or OIM (prepared with DMEM, 10% FCS, dexamethasone, β glycerol phosphate and ascorbic acid) for 21 days. Media will be changed every three days.

Following siRNA and pharmacological inhibition the effect of IDO-1 knockdown on osteogenic differentiating MSC will be characterised. After three siRNA transfections for IDO-1, the following experiments will be performed:

analysis of Runx2 nuclear binding by ELISA using the ELISA-based Runx2 activation TransAM kit (Active Motif, Rixensart, Belgium). Briefly, the Trans-AM Runx2-Kit contains a 96-well plate on which an oligonucleotide containing a AML-1 consensus-binding site (5'-AACCACA-3') that has been immobilized. Runx2-contained in nuclear extract specifically binds to this oligonucleotide. The primary antibody used in the Trans-AM Kit recognizes an accessible epitope on Runx2-protein upon DNA binding. Addition of a secondary horseradish peroxidase (HRP)-conjugated antibody provides a sensitive colorimetric readout easily quantified by spectrophotometry (450 nm). To quantify Runx2-activation, 20 μg of nuclear extract will be measured using the Trans-AM Runx2 Kit according to the manufacturer's instructions (Active Motif, Carlsbad, Calif., USA co-immunoprecipitation (CoIP) of Smads and Runx2.

measurement of enzyme activity and end products of both the kynurenine and serotonin pathways using HPLC.

Subsequently, the effect of IDO-1 knockdown on the dynamics and interactions of the elements of the Wnt/β-catenin activated pathway in differentiating MSC will be characterised. Wnts are proteins that bind to a membrane receptor complex comprised of a frizzled (FZD) G-protein-coupled receptor and a low-density lipoprotein (LDL) receptor-related protein (mostly LRP5). The formation of this ligand-receptor complex initiates a number of intracellular signalling cascades that includes the canonical/β-catenin pathway. High levels of β-catenin in the nucleus exert a potent osteogenic stimulus. In contrast, GDS inhibits this pathway by inactivating lrp5 in the duodenum without affecting β-catenin. In this set of experiments new evidence on the effect of IDO-1 inhibition on the Lrp5/β-catenin system in vitro will be generated using the following techniques:

Quantification of changes in Lrp5 and β-catenin expression both at both gene (PCR) and protein (Western blot) levels.

Colocalization of β-catenin (cytoplasmic vs. nuclear) using confocal microscopy.

Colocalization of Runx2/β-catenin using confocal microscopy and quantified using ImageJ software (NIH, USA) for image analysis.

These experiments will provide a comprehensive assessment of changes in the osteogenic response of MSC induced by lack of IDO-1 activity. Furthermore, from a mechanistic approach, the second set of experiments will attempt to identify the role of kynurenine pathway in the activation of the canonical Wnt pathway of osteoblastogenesis. Overall it is expected these experiments will verify that an absence of IDO-1 affects osteoblastogenesis, thus confirming that activation of the kynurenine pathway is essential in osteoblast differentiation and bone formation in vitro.

Finally, it will be determined whether the role of IDO-1 in bone metabolism is also exerted through an indirect (immune) mechanism.

To assess whether the anabolic effect of IDO-1 on bone formation is independent of changes in the T lymphocytes repository, osteogenic differentiating MSC will be exposed to supernatants obtained from T lymphocytes and Jurkat cells. Briefly, human T lymphocytes and Jurkat cells will be grown in niacin free PMRI media with or without IFNγ (10 nM) for one week. Supernatants will be isolated and kept at −80° C. for further experiments. Subsequently, MSC will be induced to differentiate into osteoblasts in media containing 50% of supernatants obtained from IFNγ-treated and untreated lymphocytes. After three weeks of differentiation, levels of osteoblastogenesis and activation of the kynurenine pathway will be compared between all conditions using the same techniques as described above.

The expected discovery of similarly higher levels of IDO-1 activity and osteoblastogenesis in MSC exposed to supernatants obtained from both IFNγ-treated and vehicle-treated cells will serve to confirm that activation of IDO-1 in the model utilised is independent of the presence of immune cells-secreted factors in the media.

The invention claimed is:

1. A method for treating osteoporosis in a mammalian subject comprising administering a therapeutically effective amount of picolinic acid to the subject, thereby treating the osteoporosis in the subject.

2. The method according to claim 1, wherein said method further comprises administering interferon gamma (IFNγ) to the subject.

3. The method of claim 1, wherein the osteoporosis is primary or secondary osteoporosis.

4. The method of claim 1, wherein the administering induces bone formation in the mammalian subject.

5. The method of claim 1, wherein the picolinic acid is orally administered to the subject.

* * * * *

UNITED STATES PATENT AND TRADEMARK OFFICE
CERTIFICATE OF CORRECTION

PATENT NO. : 9,642,897 B2  
APPLICATION NO. : 14/344702  
DATED : May 9, 2017  
INVENTOR(S) : Duque et al.

Page 1 of 1

It is certified that error appears in the above-identified patent and that said Letters Patent is hereby corrected as shown below:

On the Title Page

Item [73] delete:  
"THE UNIVERSITY OF SYDNEY,  
Sydney, New South Wales (AU)"

Insert:  
--NEPEAN BLUE MOUNTAINS LOCAL HEALTH DISTRICT,  
Kingswood, New South Wales (AU)--

Signed and Sealed this  
Fourth Day of September, 2018

Andrei Iancu  
*Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: forward primer specific for runt-related
      transcriptional factor 2 mRNA

<400> SEQUENCE: 1
gccgggaatg atgagaacta                                                     20

<210> SEQ ID NO 2
<211> LENGTH: 20
<212> TYPE: DNA
<213> ORGANISM: Artificial Sequence
<220> FEATURE:
<223> OTHER INFORMATION: reverse primer specific for runt-related
      transcriptional factor 2 mRNA

<400> SEQUENCE: 2
ggaccgtcca ctgtcacttt                                                     20

<210> SEQ ID NO 3
<211> LENGTH: 20
<212> TYPE: DNA
<213> ORGANISM: Artificial Sequence
<220> FEATURE:
<223> OTHER INFORMATION: forward primer specific for osteocalcin mRNA

<400> SEQUENCE: 3
cttggtgcac acctagcaga                                                     20

<210> SEQ ID NO 4
<211> LENGTH: 20
<212> TYPE: DNA
<213> ORGANISM: Artificial Sequence
<220> FEATURE:
<223> OTHER INFORMATION: reverse primer specific for osteocalcin mRNA

<400> SEQUENCE: 4
```

-continued

```
accttattgc cctcctgctt                                            20

<210> SEQ ID NO 5
<211> LENGTH: 21
<212> TYPE: DNA
<213> ORGANISM: Artificial Sequence
<220> FEATURE:
<223> OTHER INFORMATION: forward primer specific for glyceraldehyde-3-
      phosphate dehydrogenase

<400> SEQUENCE: 5
gaaatcccat caccatcttc c                                          21

<210> SEQ ID NO 6
<211> LENGTH: 20
<212> TYPE: DNA
<213> ORGANISM: Artificial Sequence
<220> FEATURE:
<223> OTHER INFORMATION: reverse primer specific for glyceraldehyde-3-
      phosphate dehydrogenase

<400> SEQUENCE: 6
aaatgagccc cagccttctc                                            20
```